US007666428B2

(12) United States Patent
Deweerd et al.

(10) Patent No.: US 7,666,428 B2
(45) Date of Patent: Feb. 23, 2010

(54) RECOMBINANT ALLERGEN WITH REDUCED IGE BINDING BUT UNDIMINISHED T-CELL ANTIGENICITY

(75) Inventors: Nicole Deweerd, Seaford (AU); Mohan Bir Singh, Templestowe (AU); Prem L. Bhalla, Templestowe (AU); Ines Swoboda, Klagenfurt (AU)

(73) Assignee: The University of Melbourne, Parkville, Victoria (AU)

( * ) Notice: Subject to any disclaimer, the term of this patent is extended or adjusted under 35 U.S.C. 154(b) by 256 days.

(21) Appl. No.: 10/490,305

(22) PCT Filed: Sep. 13, 2002

(86) PCT No.: PCT/AU02/01261

§ 371 (c)(1),
(2), (4) Date: Sep. 22, 2004

(87) PCT Pub. No.: WO03/025009

PCT Pub. Date: Mar. 27, 2003

(65) Prior Publication Data

US 2005/0074464 A1 Apr. 7, 2005

(30) Foreign Application Priority Data

Sep. 20, 2001 (AU) .................................... PR7792

(51) Int. Cl.

| | |
|---|---|
| ***A01N 37/18*** | (2006.01) |
| ***A61K 38/00*** | (2006.01) |
| ***A61K 39/00*** | (2006.01) |
| ***A61K 39/35*** | (2006.01) |
| ***A61K 39/36*** | (2006.01) |
| ***C07K 2/00*** | (2006.01) |
| ***C07K 4/00*** | (2006.01) |
| ***C07K 5/00*** | (2006.01) |
| ***C07K 7/00*** | (2006.01) |
| ***C07K 14/00*** | (2006.01) |
| ***C07K 16/00*** | (2006.01) |
| ***C07K 17/00*** | (2006.01) |

(52) U.S. Cl. ..................... 424/185.1; 424/275.1; 514/2; 530/300; 530/326

(58) Field of Classification Search ....................... None
See application file for complete search history.

(56) References Cited

FOREIGN PATENT DOCUMENTS

| | | | |
|---|---|---|---|
| CA | 2528053 | | 12/2004 |
| WO | WO 89/09260 A1 | | 10/1989 |
| WO | WO 92/03550 | * | 3/1992 |
| WO | WO 93/04174 | * | 3/1993 |
| WO | WO 93/04174 A1 | | 3/1993 |
| WO | WO 94/04564 | * | 3/1994 |
| WO | WO 95/06728 | * | 3/1995 |
| WO | WO-95/06728 A1 | | 3/1995 |
| WO | WO 2004/108758 | | 12/2004 |

OTHER PUBLICATIONS

Schramm et al. ""'Allergen Engineering": Variants of the Timothy Grass Pollen Allergen Phl p 5b with Reduced IgE-Binding Capacity but Conserved T Cell Reactivity. ' J. Immunol. 162:2406-2414, 1999.*

Suphioglu et al. 'Molecular cloning, expression and immunological characterisation of Lol p 5C, a novel allergen isoform of rye grass pollen demonstrating high IgE reactivity.' FEBS 462:435-441, 1999.*

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*

Blumenthal et al. 'Definition of an Allergen.' Allergens and Allergen Immunotherapy. Ed. R Lockey, S. Bukantz and J. Bousquet. New York: Marcel Decker, 2004. 37-50.*

Skolnick et al. 'From genes to protein structure and function: novel applications of computational approaches in the genomic era.' Trends in Biotech. 18:34-39, 2000.*

Attwood et al. 'The Babel of Bioinformatics.' Science. 290(5491):471-473.*

Burgess et al. 'Possible Dissociation of the Heparin-binding and Mitogenis Activities of Heparin-binding (Acidis Fibroblast) Growth Factor-1 from Its Receptor-binding Activites by Site-directed Mutagenesis of a Single Lysine Residue.' J. Cell. Biol. 111:2129-2138, 1990.*

Lazar et al. 'Transforming Growth Factor alpha:Mutation of Aspartic Acid 47 and Leucine 48 Results in Different Biological Activities.' Mol. Cell. Biol. 8(3):1247-1252, 1988.*

Bowie et al. 'Deciphering the message in protein sequences: tolerance to amino acid substitutions.' Science. 247(4948)1306-1310.*

Blumenthal et al, in Allergens and Allergen Immunotherapy, 3rd edition, 2004, pp. 37-51.*

Burk et al, Eur. J Biochem 245(2): 334-9, Apr. 1997.*

Bose, et al. Production and characterization of mouse monoclonal antibodies to allergenic epitopes on Lolpl (Rye I). Immunology. Oct. 1986;59(2):309-15.

(Continued)

*Primary Examiner*—Maher M Haddad
*Assistant Examiner*—Nora M Rooney
(74) *Attorney, Agent, or Firm*—Arent Fox LLP

(57) ABSTRACT

The present invention relates generally to reagents useful in the immunotherapeutic or immunoprophylactic treatment of allergic diseases. More particularly, the present invention provides modified allergens exhibiting reduced IgE interactivity including reduced IgE production-stimulatory activity, while retaining T-cell antigenicity, which are useful in the immunomodulation of type I allergic disease conditions. The present invention further contemplates a method of immunomodulation of allergic diseases such as type I allergic disease conditions by the administration of modified allergens exhibiting reduced IgE interactivity while retaining T-cell antigenicity.

3 Claims, 8 Drawing Sheets

OTHER PUBLICATIONS

Brieva, et al. Rapid purification of the main allergen of *Lolium perenne* by high-performance liquid chromatography. J Chromatogr. Nov 26, 1986;370(1):165-72.

Chakrabarty S, et al. Detection of cross-reactive allergens in Kentucky bluegrass pollen and six other grasses by crossed radioimmunoelectrophoresis. Int Arch Allergy Appl Immunol. 1981;66(2):142-57.

Cook, et al. Induction of allergen-specific T cells by conjugates of N-formyl-methionyl-leucyl-phenylalanine and rye grass pollen extract. Int Arch Allergy Appl Immunol. 1988;85(1):104-8.

Cornford, et al. IgE-binding proteins from pine (Pinus radiata D. Don) pollen: evidence for cross-reactivity with ryegrass (*Lolium perenne*). Int Arch Allergy Appl Immunol. 1990;93(1):41-6.

Cottam, et al. Physicochemical and immunochemical characterization of allergenic proteins from rye-grass (*Lolium perenne*) pollen prepared by a rapid and efficient purification method. Biochem J. Mar. 1, 1986;234(2):305-10.

Cottam, et al. Immunological properties of chemically produced fragments of rye grass pollen extract. Immunol Lett. Apr. 1988;17(4):345-9.

Ellis. New Technologies for Making Vaccines. Vaccines. 1988, W.B. Saunders Company. pp. 568-575.

Esch, et al. Isolation and characterization of a major cross-reactive grass group I allergenic determinant. Mol Immunol. Jun. 1989 ;26(6):557-61.

Freidhoff, et al. A study of the human immune response to Lolium perenne (rye) pollen and its components, Lol p I and Lol p ll (Rye I and Rye II). II. Longitudinal variation of antibody levels in relation to symptomatology and pollen exposure and correction of seasonally elevated antibody levels to basal values. J Allergy Clin Immunol. Nov. 1987;80(5):646-55.

Freidhoff, et al. A study of the human immune response to Lolium perenne (rye) pollen and its components, Lol p I and Lol II (rye I and rye II). I. Prevalence of reactivity to the allergens and correlations among skin test, IgE antibody, and IgG antibody data. J Allergy Clin lmmunol. Dec. 1986;78(6):1190-201.

Freidhoff, et al. Association of HLA-DR3 with human immune response to Lol p I and Lol p II allergens in allergic subjects. Tissue Antigens. Apr. 1988;31(4):211-9.

Griffith, et al. Cloning and sequencing of Lol pI, the major allergenic protein of rye-grass pollen. FEBS Lett. Feb. 25, 1991;279(2):210-5.

Hatton, et al. Molecular Cloning of Kentucky Bluegrass Pollen Allergens. J. Allergy Innumology. 1988. 81(1):183.

Hill, et al. Specific cellular and humoral immunity in children with grass pollen asthma. Clin Allergy. Jan. 1982;12(1):83-9.

Hopp, et al. Prediction of protein antigenic determinants from amino acid sequences. Proc. Natl Acad Sci U S A. Jun. 1981;78(6):3824-8.

Howlett, et al. Cross-reactivity between Acacia (wattle) and rye grass pollen allergens. Detection of allergens in Acacia (wattle) pollen. Clin Allergy. May 1982;12(3):259-68.

Kahn, et al. Monoclonal antibodies to the major *Lolium perenne* (rye grass) pollen allergen Lol p I (Rye l). Mol Immunol. Dec. 1986;23(12):1281-8.

Klysner, et al. Group V allergens in grass pollens: IV. Similarities in amino acid compositions and NH2-terminal sequences of the group V allergens from *Lolium perenne*, Poa pratensis and Dactylis glomerata. Clin Exp Allergy. Apr. 1992;22(4):491-7.

Kumar, et al. Amino acid variations at a single residue in an autoimmune peptide profoundly affect its properties: T-cell activation, major histocompatibility complex binding, and ability to block experimental allergic encephalomyelitis. Proc Natl Acad Sci U S A. Feb. 1990;87(4):1337-41.

Lin, et al. Isolation and characterization of Poa p I allergens of Kentucky bluegrass pollen with a murine monoclonal anti-Lol p I antibody. Int Arch Allergy Appl Immunol. 1988;87(3):294-300.

Lin, et al. Mapping of epitopes on Poa p I and Lol p I allergens with monoclonal antibodies. Int Arch Allergy Appl Immunol. 1990:91(3):217-23.

Lowenstein, et al. Immunological partial identity and in vitro inhibitory effect of two major timothy pollen allergens to whole pollen extract of four grasses. Int Arch Allergy Appl Immunol. 1978:57(4):379-83.

Lowenstein, et al. Isolation and partial characterization of three allergens of timothy pollen Allergy. Feb. 1978;33(1):30-41.

Lowenstein, et al. Timothy pollen allergens. Allergy. Apr. 1980;35(3):188-91.

Lowenstein, et al. Purification of timothy pollen allergens followed by quantitative immunoelectrophoresis. Int Arch Allergy Appl lmmunol. 1975;49(1-2):95-8.

Margalit, et al. Prediction of immunodominant helper T cell antigenic sites from the primary sequence. J Immunol. Apr. 1, 1987;138(7):2213-29.

Marsh, et al. Induction of IgE-mediated immediate hypersensitivity to group I rye grass pollen allergen and allergoids in non-allergic man. Immunology. Jun. 1972;22(6):1013-28.

Martin, et al. Cross-allergenicity among the grasses. Ann Allergy. Feb. 1985 ;54(2):99-104.

Matthiesen, et al. Group V allergens in grass pollens. I. Purification and characterization of the group V allergen from Phleum pratense pollen, Phl p V. Clin Exp Allergy. May 1991;21(3):297-307.

Matthiesen, et al. Group V allergens in grass pollens. II. Investigation of group V allergens in pollens from 10 grasses. Clin Exp Allergy. May 1991;21(3):309-20.

Mecheri, et al. Purification and characterization of a major allergen from Dactylis glomerate pollen: the Ag Dg1. Int Arch Allergy Appl Immunol. 1985;78(3):283-9.

Mohapatra, et al. Isolation and characterization of a cDNA clone encoding an IgE-binding protein from Kentucky bluegrass (Poa pratensis) pollen. Int Arch Allergy Appl Immunol. 1990;91(4):362-8.

Mourad, et al. Allergenicity and cross-reactivity of rye grass pollen extracts revealed by monoclonal antibodies. J Immunol Methods. May 1, 1986;89(1):53-9.

Mourad, et al. Study of the epitope structure of purified Dac G I and Lol p I, the major allergens of Dactylis glomerata and Lolium perenne pollens, using monoclonal antibodies. J Immunol. Nov. 15, 1988;141(10):3486-91.

Mourad, et al. Mapping of Lol p I allergenic epitopes by using murine monoclonal antibodies. Mol Immunol. Nov. 1989;26(11):1051-7.

Olsen, et al. Identification and characterization of the Poa p IX group of basic allergens of Kentucky bluegrass pollen. J Immunol. Jul. 1, 1991;147(1)205-11.

Perez, et al. cDNA cloning and immunological characterization of the rye grass allergen Lol p I. J Biol Chem. Sep. 25, 1990;265(27):16210-5.

Silvanovich, et al. Nucleotide sequence analysis of three cDNAs coding for Poa p IX isoallergens of Kentucky bluegrass pollen. J Biol Chem. Jan. 15, 1991;266(2):1204-10.

Singh, et al. Isolation of cDNA encoding a newly identified major allergenic protein of rye-grass pollen: intracellular targeting to the amyloplast. Proc Natl Acad Sci U S A. Feb. 15, 1991;88(4):1384-8.

Singh, et al. Molecular biology of rye-grass pollen allergens. Monogr Allergy. 1990;28:101-20.

Singh, et al. Grass pollen allergens: antigenic relationships detected using monoclonal antibodies and dot blotting immunoassay. Int Arch Allergy Appl lmmunol. 1985;78(3):300-4.

Smart, et al. Rapid batch fractionation of ryegrass pollen allergens. Int Arch Allergy Appl Immunol. 1980;62(2)179-87.

Smart, et al. Development of monoclonal mouse antibodies specific for allergenic components in ryegrass (*Lolium perenne*) pollen. Int Arch Allergy Appl Immunol. 1983;72(3):243-8.

Standring, et al. Distribution of a major allergen of rye grass (*Lolium perenne*) pollen between other grass species. Int Arch Allergy Appl Immunol. 1987;83(1):96-103.

Standring, et al. Induction of T-helper cell activity by fragments of rye grass pollen extract produced by digestion with chymotrypsin. Int Arch Allergy Appl Immunol. 1988;87(4):337-41.

Van Hage-Hamsten, et al. Differences in the Allergenic Cross-reactivity Patterns Between Non Pyroglyphid and Pyroglyphid Mites in Two Populations. J. Allergy Clin. Immunol. 1990. 85:279.

Van Ree, et al. Characterization with monoclonal and polyclonal antibodies of a new major allergen from grass pollen in the group I molecular weight range. J Allergy Clin Immunol. Jan. 1989;83(1):144-51.

Ventas, et al. OP46: Monoclonal Antibodies to a Major Allergen from Lepidoglyphus Destructor. Clin. Experimental Allergy. 1990. 20:47.

Vithanage et al. Immunocytochemical localization of water-soluble glycoproteins, including group 1 allergen, in pollen of ryegrass, *Lolium perenne*, using ferritin-labelled antibody. Histochem J. Nov. 1982;14(6):949-66.

Walsh, et al. Cloning of cDNA coding for an allergen of Cocksfoot grass (*Dactylis glomerata*) pollen. Int Arch Allergy Appl Immunol. 1989;90(1):78-83.

Walsh, et al. Monoclonal antibodies to proteins from cocksfoot grass (*Dactylis glomerata*) pollen: isolation and N-terminal sequence of a major allergen. Int Arch Allergy Appl Immunol. 1990;91(4):419-25.

Wheeler, et al. Retained T-cell reactivity of rye grass pollen extract following cleavage with cyanogen bromide and nitrothiocyanobenzoic acid. Int Arch Allergy Appl Immunol. 1988;86(1):1-8.

Zhang, et al. Crossreactivity and Variable Allergenicity of a Poa p IX Allergen. J. Allergy. 1991. 87:325.

Blaher, Bella et al, "Identification of T-cell epitopes of Lol p 9, a major allergen of ryegrass (*Lolium perenne*) pollen," *J. Allergy Clin. Immunol.*, vol. 98:124-132 (1996).

Burton, Matthew D. et al, "T-cell receptor contact and MHC binding residues of a major rye grass pollen allergen T-cell epitope," *J. Allergy Clin. Immunol.*, vol. 103:255-261 (1999).

de Lalla, Claudia et al, "Cutting Edge: Identification of Novel T Cell Epitopes in Lol *p*5a by Computational Prediction," *The Journal of Immunology*, vol. 163:1725-1729 (1999).

Ong, Eng Kok et al, "Cloning of a cDNA encoding a group-V (group-IX) allergen isoform from rye-grass pollen that demonstrates specific antigenic immunoreactivity," *Gene*, vol. 134:235-240 (1993).

Ong, E.K. et al, "Mapping of the Antigenic and Allergenic Epitopes of *Lol p*VB Using Gene Fragmentation," *Molecular Immunology*, vol. 32(4):295-302 (1995).

Suphioglu, Cenk et al, "Molecular basis of IgE-recognition of Lol p 5, a major allergen of rye-grass pollen," *Molecular Immunology*, vol. 35:293-305 (1998).

Swoboda, Ines et al, "Mutants of the major ryegrass pollen allergen, Lol p 5, with reduced IgE-binding capacity: candidates for grass pollen-specific immunotherapy," *Eur. J. Immunol.*, vol. 32:270-280 (2002).

Swoboda, Ines et al, "Hypoallergenic Forms of the Ryegrass Pollen Allergen Lol p 5 as Candidates for Immunotherapy," *International Archives of Allergy and Immunology*, vol. 124:380-382 (2001).

European Search Report for Application No. 02757980.4-2401, dated May 12, 2006.

Schramm G. et al., "Allergen engineering": Variants of the timothy grass pollen allergen Ph1 p 5B with reduced IgE-binding capacity but not conserved T cell reactivity, The Journal of Immunology, Feb. 15, 1999, vol. 162(4), pp. 2406-2414, XP002216586.

Muller, W.D., et al., Allergologie, vol. 22, No. 8 (Aug. 1999), "T-zell epitope von allegnenen", pp. 455-459.

Wiedermann U. et al., International Archives of Allergy and Immunology, vol. 124 (2001), "Mucosal tolerance induction with hypoallergenic molecules in a murine model of allergic asthma", pp. 391-394.

Bannon, G.A., et al., International Archives of Allergy and Immunology, vol. 124 (2001), "Engineering, characterization and in vitro efficacy of the major peanut allergens for use in immunotherapy", pp. 70-72.

Akdis, C.A., et al., International Archives of Allergy and Immunology, vol. 121 (2000), "Regulation of specific immune responses by chemical and structural modifications of allergens", pp. 261-269.

Son, D.Y., et al., European Journal of Nutrition, vol. 38 (1999), "Pollen-related food allergy: cloning and immunological analysis of isoforms and mutants of Mal d 1, the major apple allergen, and Bet v 1, the maior birch pollen allergen", pp. 201-215.

Kraft, D., et al., international Archives of Allergy and Immunology, vol. 118 (1999), "The importance of recombinant allergens for diagnosis and therapy of IgE-mediated allergies", pp. 171-176.

Larche, M., et al., Progress in Respiratory Research, vol. 31 (2001), "Allergen, IgE and mast-cell-directed therapies: an overview", pp. 182-185.

Takai, T., et al., Molecular Immunology, vol. 36 (1999), "Non-anaphylactic combination of partially deleted fragments of the major house dust mite allergen Der f for allergen-specific immunotherapy", Molecular Immunology, pp. 1055-1065.

\* cited by examiner

```
Lol p 5 A      ADAGYTPAAAATPATPAATPAAA------------GGKATTDEQKLLEDVN   [SEQ ID NO:1]
Lol p 5 B      *****A**TP****A**TAATP*TPATPATPAAVPS*****E****I*KI*   [SEQ ID NO:2]
Phl p 5 A      **L**G**TP*----***GYTP*TPAAPAGADAA--*****E****I*KI*   [SEQ ID NO:3]
Phl p 5 B      *****------A******AG***-------------*****E****I*KI*   [SEQ ID NO:4]
Poa p 5 (41)   **V**GAP*TL--****TP***PAAGYTPAAPAGAAP*********I*KI*   [SEQ ID NO:5]
Poa p 5 (60)   **LS*GAP*T---------***PAAGYTPAAPAGAAP********MI*KI*   (SEQ ID NO:6]

Lol p 5 A      AGFKAAVAAAANAPPADKFKIFEAAFSESSKGLLATSAAKAPG--------   [SEQ ID NO:1]
Lol p 5 B      ***********VV*****Y*T*VET*G--------*ATN**FVEGLASGYA   [SEQ ID NO:2]
Phl p 5 A      ******L*G*GVQ-****YRT*V*T*GPA*--------N**FAEGLSGEPK   [SEQ ID NO:3]
Phl p 5 B      V********R--Q*A*****T****SPRHPRP*RQGAG-------------   [SEQ ID NO:4]
Poa p 5 (41)   ***********GV*AV**Y*T*V*T*G--------*ASN**FAEALSTEPK   [SEQ ID NO:5]
Poa p 5 (60)   V*********GGV*A*N*Y*T*V*T*G--------AASN**FAEALSTEPK   [SEQ ID NO:6]

Lol p 5 A      ----------LIPKLDTAYDVAYKAAEGATPEAKYDAFVTALTEALRVIAG   [SEQ ID NO:1]
Lol p 5 B      ----DQSKNQ*TS***A*LKL**E**Q**********Y*AT**********   [SEQ ID NO:2]
Phl p 5 A      GAAESSSKAA*TS***A**KL***T************Y*AT*S****I***   [SEQ ID NO:3]
Phl p 5 B      ----------*VS***A**S******V*******F*S**AS**********   [SEQ ID NO:4]
Poa p 5 (41)   GAAAASSNAV*TS***A**KL***S************YVATLS****I***   [SEQ ID NO:5]
Poa p 5 (60)   GAAADSSKAA*TS***A**KL***S***********DY*AT*S****I***   [SEQ ID NO:6]

Lol p 5 A      ALEVHAVKPATEEVPAAKIPTGELQIVDKIDAAFKIAATAANAAPTNDKFT   [SEQ ID NO:1]
Lol p 5 B      T*********A***KVGA**AA*V*LI**V***YRT*********A*****   [SEQ ID NO:2]
Phl p 5 A      T*********A***KV--**A****VIE*V*****V*********A*****   [SEQ ID NO:3]
Phl p 5 B      *********V***PGM****A*****I********V*****AT**AD****   [SEQ ID NO:4]
Poa p 5 (41)   T*********G***K--A**A****VI**V*****V*********A*****   [SEQ ID NO:5]
Poa p 5 (60)   T****G****A***K--AT*A****VI**V*****V*********A*****   [SEQ ID NO:6]
```

Figure 1

```
Lol p 5 A      VFESAFNKALNECTGGAYETYKFIPSLEAAVKQAYAATVAAAPEVKYAVFE    [SEQ ID NO:1]
Lol p 5 B      ***NT**N*IKVSL*A**DS*****TLV*********KQ*T******T*S*    [SEQ ID NO:2]
Phl p 5 A      ***A***DEIKAS******S*****A**************T******T***    [SEQ ID NO:3]
Phl p 5 B      ***A*****IK*S*****D***C*******************A****T***    [SEQ ID NO:4]
Poa p 5 (41)   ***A***D*IKAS*****QS*****A*******S******T**A*******    [SEQ ID NO:5]
Poa p 5 (60)   ***A***D*IKAS*****QS*****A*******S******T**A*******    [SEQ ID NO:6]

Lol p 5 A      AALTKAITAMTQAQKAGKPAAAA-------------------ATGAATVAT    [SEQ ID NO:1]
Lol p 5 B      T**K**V***SE*E*EAT*****TATPTPAAATATATPAAAY*TATPAA**    [SEQ ID NO:2]
Phl p 5 A      T**K******SE****A**PPLPPPPQPPPL--------------------    [SEQ ID NO:3]
Phl p 5 B      **********SEV*SKVQ*-----------------------********A    [SEQ ID NO:4]
Poa p 5 (41)   T**K******S*****A*****V---------TATATGAVGA****VGA**    [SEQ ID NO:5]
Poa p 5 (60)   T**K******S*****A******---------TGTATAAVGA****-----    [SEQ ID NO:6]

Lol p 5 A      GAATAAAGAA-----TAAAGGYKA                               [SEQ ID NO:1]
Lol p 5 B      *T**P**AT*----TP*******V                               [SEQ ID NO:2]
Phl p 5 A      -----**AG*----A***T****V                               [SEQ ID NO:3]
Phl p 5 B      ****T*****-SGAA*V******V                               [SEQ ID NO:4]
Poa p 5 (41)   ********GYKTGAA*PT*****V                               [SEQ ID NO:5]
Poa p 5 (60)   --------------A********V                               [SEQ ID NO:6]
```

Figure 1 continued

[SEQ ID NO:7]

```
      MAVQKYTVALFLAVALVAGPAASYA
-25
                              A
   ADAGYTPAAAATPATPAATPAAAGGKATTDEQKLLEDVNAGFKAAVAAANAPPADKFKI      60
 1                                                         D1
   FEAAFSESSKGLLATSAAKAPGLIPKLDTAYDVAYKAAEGATPEAKYDAFVTALTEALRV    120
61
                                          NLAA
   IAGALEVHAVKPATEEVPAAKIPTGELQIVDKIDAAFKIAATAANAAPTNDKFTVFESAF    180
121                                                    D4
                      GAA                  A A
   NKALNECTGGAYETYKFIPSLEAAVKDAYAATVAAAPEVKYAVFEAALTKAITAMTQAQK    240
181                      D5                          GGYKA
                                                      D3 D2
   AGKPAAAAATGAATVATGAATAAAGAATAAA                                301
241
```

Figure 2

| NAME | SEQUENCE (5' → 3') |
|---|---|
| D1 fwd | CCTCCGGCGGACGCGTTCAAGATC [SEQ ID NO:13] |
| D1 rev | GATCTTGAACGCGTCCGCCGGAGG [SEQ ID NO:14] |
| D2 fwd | GCTGCTGGTGCCTACGCAGCCTGATCAGC [SEQ ID NO:15] |
| D2 rev | GCTGATCAGGCTGCGTAGGCACCAGCAGC [SEQ ID NO:16] |
| D3 fwd | CCACCGCCGCTGCTTGAGGCTACAAAGC [SEQ ID NO:17] |
| D3 rev | GCTTTGTAGCCTCAAGCAGCGGCGGTGG [SEQ ID NO:18] |
| D4 fwd | CCACCAACGATAACTTGGCCGCCTTCGAGAGTGC [SEQ ID NO:19] |
| D4 rev | GCACTCTCGAAGGCGGCCAAGTTATCGTTGGTGG [SEQ ID NO:20] |
| D5 fwd | CCTCGAGGCCGGGGCCGCGCAGGCCTACG [SEQ ID NO:21] |
| D5 rev | CGTAGGCCTGCGCGGCCCCGGCCTCGAGG [SEQ ID NO:22] |

Figure 4

RECOMBINANT ALLERGEN WITH REDUCED IGE BINDING BUT UNDIMINISHED T-CELL ANTIGENICITY

RELATED APPLICATIONS

This application is a 35 U.S.C. 371 national stage filing of International Application No. PCT/AU02/01261, filed 13 Sep. 2002, which claims priority to Australian Patent Application No. PR 7792 filed on 20 Sep. 2001 in Australia. The contents of the aforementioned applications are hereby incorporated by reference.

FIELD OF THE INVENTION

The present invention relates generally to reagents useful in the immunotherapeutic or immunoprophylactic treatment of allergic diseases. More particularly, the present invention provides modified allergens exhibiting reduced IgE interactivity including reduced IgE production-stimulatory activity, while retaining T-cell antigenicity, which are useful in the immunomodulation of type I allergic disease conditions. The present invention further contemplates a method of immunomodulation of allergic diseases such as type I allergic disease conditions by the administration of modified allergens exhibiting reduced IgE interactivity while retaining T-cell antigenicity.

BACKGROUND OF THE INVENTION

Bibliographic details of references provided in the subject specification are listed at the end of the specification.

Reference to any prior art in this specification is not, and should not be taken as, an acknowledgment or any form of suggestion that this prior art forms part of the common general knowledge in any country.

Type I allergic diseases such as seasonal allergic rhinitis (hayfever), conjunctivitis, allergic asthma and allergic dermatitis represent a major health problem in industrialized countries (Wuthrich, *Int. Arch. Allergy Immunol.* 90: 3-10, 1989). It is currently estimated that 15-20% of the population in developed countries are afflicted with some form of allergy (Miyamoto, *Advances in Allergology and Clinical Immunology*. Godard P, Bousquet J, Michel F B (eds) pp. 343-347. The Parthenon Publishing Group, Cornforth, UK, 1992). Therefore, the diagnosis and therapy of these diseases have become focal points of interest for scientific investigation.

The primary immunological and biochemical bases of type I allergic reactions are the interaction of allergenic substances (allergens) with IgE antibodies bound to high affinity Fc receptors on the surface of mast cells and basophils. This interaction results in cross linking of allergen-specific IgE antibodies which in turn stimulates an immediate release and cascade production of inflammatory mediators responsible for allergic symptoms. Allergens are present in airborne particles such as house-dust, pollen of grasses, weeds and trees, mould spores and animal dander.

At present, one form of therapeutic intervention of allergic diseases (such as rhinitis, conjunctivitis and allergic asthma) involves injection of the allergen assumed to be responsible for the allergic response. This is referred to as hypo-sensitization treatment. Extracts currently in use in this procedure are prepared from natural sources and contain, in addition to the allergens, components such as proteins to which patients are not allergic.

The development of recombinant techniques has provided the means to produce high levels of purified allergens for diagnostic and therapeutic purposes. However, the high level of purity of recombinant allergen preparations results in a high anaphylactogenic index even at very low doses. Accordingly, extreme care is required when they are administered to patients. There is a need, therefore, to develop recombinant allergens with a reduced risk of anaphylactic shock.

The major outdoor cause of seasonal hay-fever and allergic asthma is airborne grass pollen (Smart et al., *Int. Arch. Allergy Immunol.* 7: 243-248, 1983). Pollen calendars show that grass pollen is most abundant in spring and early summer when grasses flower and this is when allergic asthma peaks in incidence. The most important sources of grass pollen are common agricultural pasture grasses which have been widely introduced throughout the world, but vary in temperature and tropical climate zones. In cool temperature regions, grasses such as rye-grass, Kentucky bluegrass and timothy (all belonging to the subfamily Pooideae) are of clinical significance, whereas in warm temperature and subtropical environments pollen of Bermuda grass (subfamily Chloridoideae) becomes the most important source of allergens. The most comprehensive studies have been made on proteins from rye-grass pollen and to a lesser extent Kentucky bluegrass and timothy.

Individuals sensitive to allergens from one grass are often sensitive to those of a number of other grass genera. This is particularly true for pollen of grasses within the subfamily Pooideae (Smith et al., "*Analysis of rye-grass pollen allergens using two dimensional electrophoresis and immunoblotting*." In Kraft D (ed), Molecular Biology and Immunology of Allergens, CRC Press, Boca Raton, Fla., 1994), where immunological cross-reactivity has been demonstrated in inhibition experiments using an IgE-binding assay, the radioallergosorbent test (RAST). In these experiments, pollen extracts from one grass were able to inhibit binding of IgE to extracts from other grasses.

Allergenic components of grass pollen can be classified into different groups according to their physiochemical and immunological properties. The major allergens that elicit an allergic reaction to pollen from the Pooid grasses are group 1 and 5 allergens, as judged by both criteria of the number of allergic patients responding and relative amounts of IgE binding to the allergens (Singh et al, 1991, supra). In case of perennial rye-grass, *Lolium perenne*, pollen extracts contain more than 17 proteins which have the capacity to bind IgE from sera of grass pollen allergic patients (Smith et al., 1993, supra). However, it has been shown that allergens of group 1 and 5 together can inhibit most of the IgE binding to crude pollen extracts (Bond et al., *J. Allergy Clin. Immunol.* 91: 339, 1993).

Lol p 5, a protein of 28-33 kDa, is the second most prevalent rye-grass allergen which causes allergy in 85-90% of grass pollen allergic individuals. Molecular cloning of cDNAs encoding this group 5 allergen (Singh et al., *Proc. Natl. Acad. Sci. USA* 88: 1384-1388, 1991; Ong et al., *Gene* 134: 235-240, 1993) has shown that Lol p 5 exists as a family of homologous but distinguishable isoforms which retain their IgE reactivity even after separation on denaturing SDS-PAGE gels and immunoblotting (Singh et al., 1991, supra).

A need, accordingly, exists to develop modified forms of recombinant allergens useful in immunotherapy and immunoprophylaxis of allergic conditions.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention provides a modified recombinant allergen, wherein in naturally occurring form, the allergen is associated with allergic disease conditions in sensitive subjects. Conveniently, the modified recombinant allergen comprises an amino acid sequence modified from the naturally occurring amino acid sequence such that the allergen lacks or comprises reduced numbers of IgE epitopes and/or exhibits reduced binding capacity for IgE and/or exhibits reduced IgE production-stimulatory activity while retaining T-cell antigenicity.

Preferably, the allergic disease condition is a type I allergic disease condition.

Preferably, the recombinant allergen is a grass pollen allergen.

Most preferably, the grass allergen is a rye-grass pollen allergen such as but not limited to Lol p 5 or immunologically or botanically related allergens such as Phl p 5 and Poa p 5.

In a particularly preferred embodiment, the present invention provides a modified Lol p 5 allergen which lacks or comprises a reduced number of IgE epitopes and/or exhibits reduced IgE binding capacity and/or exhibits reduced IgE production-stimulatory activity while retaining T-cell antigenicity wherein said Lol p 5 variant is selected from a molecule having the amino acid sequence set forth in SEQ ID NOS:8 to 12 (see Table 1) or a modified allergen corresponding to an immunologically or botanically related allergen.

The present invention is further directed to a composition comprising a modified allergen such as a grass allergen (e.g. a rye-grass pollen allergen) which lacks or comprises reduced numbers of IgE epitopes and/or exhibits reduced binding capacity for IgE and/or exhibits reduced IgE production-stimulatory activity while retaining T-cell antigenicity. The composition further comprises one or more pharmaceutically acceptable carriers and/or diluents.

The present invention further contemplates a method for the prophylaxis or treatment of an allergic disease condition in a subject by administering to the subject, an effective amount of a modified allergen which lacks or comprises reduced numbers of IgE epitopes and/or exhibits reduced binding capacity for IgE and/or exhibits reduced IgE production-stimulatory activity while retaining T-cell antigenicity.

A summary of sequence identifiers used throughout the subject specification is provided in Table 1.

TABLE 1

Summary of sequence identifiers

| SEQUENCE ID NO: | DESCRIPTION |
|---|---|
| 1 | Amino acid sequence of isoform A of Lol p 5 |
| 2 | Amino acid sequence of isoform B of Lol p 5 |
| 3 | Amino acid sequence of isoform A of Phl p 5 |
| 4 | Amino acid sequence of isoform B of Phl p 5 |
| 5 | Amino acid sequence of isoform Poa p 5 |

TABLE 1-continued

Summary of sequence identifiers

| SEQUENCE ID NO: | DESCRIPTION |
|---|---|
| 6 | Amino acid sequence of isoform Poa p5 |
| 7 | Amino acid sequence of Lol p 5 variant |
| 8 | Amino acid sequence of Lol p 5 variant D1 |
| 9 | Amino acid sequence of Lol p 5 variant D2 |
| 10 | Amino acid sequence of Lol p 5 variant D3 |
| 11 | Amino acid sequence of Lol p 5 variant D4 |
| 12 | Amino acid sequence of Lol p 5 variant D5 |
| 13 | Nucleotide sequence of forward primer used to clone out D1 |
| 14 | Nucleotide sequence of reverse primer used to clone out D1 |
| 15 | Nucleotide sequence of forward primer used to clone out D2 |
| 16 | Nucleotide sequence of reverse primer used to clone out D2 |
| 17 | Nucleotide sequence of forward primer used to clone out D3 |
| 18 | Nucleotide sequence of reverse primer used to clone out D3 |
| 19 | Nucleotide sequence of forward primer used to clone out D4 |
| 20 | Nucleotide sequence of reverse primer used to clone out D4 |
| 21 | Nucleotide sequence of forward primer used to clone out D5 |
| 22 | Nucleotide sequence of reverse primer used to clone out D5 |

BRIEF DESCRIPTION OF THE FIGURES

FIG. 1 is a representation showing a comparison of deduced amino acid sequences of group 5 allergens. Dashes indicate gaps which have been introduced to give maximum alignment. Residues identical to Lol p 5 A are indicated by asterisks.

FIG. 2 is a representation showing amino acid sequence of Lol p 5 A indicating the mutations introduced in the allergen to give D1 (SEQ ID NO: 8), D2 (SEQ ID NO: 9), D3 (SEQ ID NO: 10), D4 (SEQ ID NO: 11) and D5 (SEQ ID NO: 12) mutants. Amino acids of Lol p 5 A that were changed are indicated by boxes, whereas new sequences are given in bold.

FIG. 4 is a representation showing sequences of primers used to create mutations in Lol p 5 A.

DETAILED DESCRIPTION OF THE PREFERRED EMBODIMENTS

Figure 3:
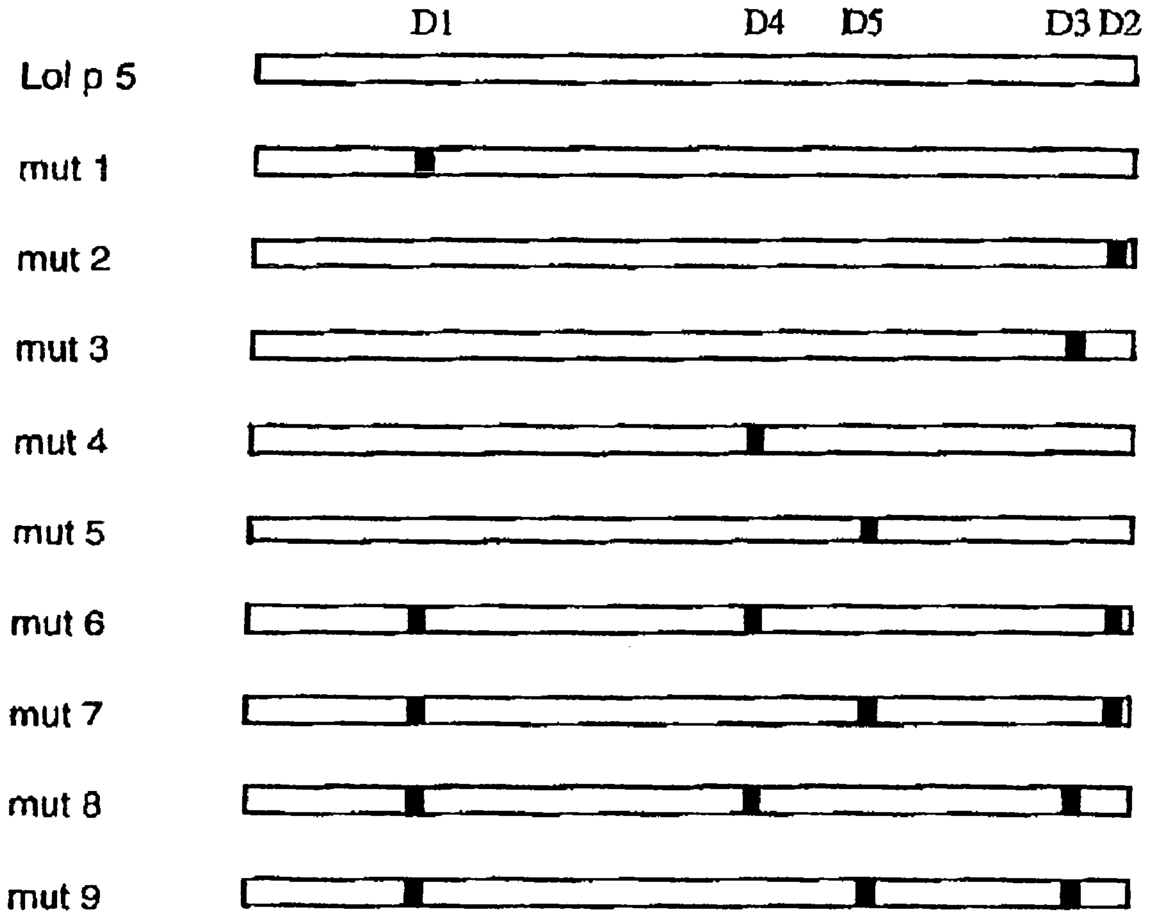
FIG. 3 is a schematic representation of mutated Lol p 5 variants; e.g. mut 1 contains mutation D1.

In accordance with the present invention, genetically engineered substantially hypoallergenic, variants of allergens with an inability or reduced capacity to interact with IgE are provided for use in immunotherapy and immunoprophylaxis. Certain types of modifications of the amino acid sequence are determined to result in a lack of or reduced numbers of IgE epitopes, reduced activity of IgE epitopes, reduced ability to interact with IgE and/or reduced IgE production-stimulatory activity.

Accordingly, one aspect of the present invention provides a modified recombinant allergen, wherein said allergen in naturally occurring form is associated with allergic disease conditions in sensitive subjects, wherein said modified recombinant allergen comprises an amino acid sequence modified from the naturally occurring amino acid sequence such that the allergen lacks or comprises reduced numbers of IgE epitopes and/or exhibits reduced binding capacity for IgE and/or exhibits reduced IgE production-stimulatory activity while retaining T-cell antigenicity.

The term "sensitive" subject is used in its broadest sense to include an individual exhibiting the symptoms of an allergic disease and more particularly a type I allergic disease in response to or associated with the allergen. An "individual" is preferably a human but also extends to a non-human primate, livestock animal (e.g. sheep, cow, pig, horse, donkey, goat), laboratory test animal (e.g. mouse, rat, rabbit, guinea pig) and a companion animal (e.g. dog, cat).

The present invention is particularly directed to grass pollen allergens.

Accordingly, another aspect of the present invention is directed to a modified recombinant grass pollen allergen, wherein said grass pollen allergen in naturally occurring form is associated with type I allergic disease-conditions wherein said modified recombinant grass pollen allergen comprises an amino acid sequence modified from the naturally occurring amino acid sequence such that the allergen lacks and/or comprises reduced numbers of IgE epitopes or exhibits reduced binding capacity for IgE and/or exhibits reduced IgE production-stimulatory activity while retaining T-cell antigenicity.

In a particularly preferred embodiment, the grass pollen allergen is a rye-grass or immunologically related grass pollen allergen such as but not limited to Lol p 5, Ph1 p 5 and Pao p 5. Reference to "grass pollen allergen" includes all rye-grass or immunologically related grass pollen allergens or other grass allergens.

Accordingly, this aspect of the present invention contemplates a modified recombinant rye grass pollen allergen comprising an amino acid sequence modified from the naturally occurring amino acid sequence such that the allergen lacks or comprises reduced numbers of IgE epitopes and/or exhibits reduced binding capacity for IgE and/or exhibits reduced IgE production-stimulatory activity while retaining T-cell antigenicity.

The retention of T-cell antigenicity includes reference to the retention of T-cell epitopes or an otherwise capacity to interact with T cells to elicit a T-cell response.

The present invention is hereinafter described in relation to Lol p 5. This is done since Lol p 5, up to the present time, represents a particularly useful allergen in which to practice the present invention. This is done, however, with the understanding that the present invention extends to any allergen, especially an allergen involved in type I allergic diseases such as but not limited to a group 5 grass pollen allergen. The methods of the present invention are particularly applicable to any rye-grass or immunologically related grass pollen allergen in addition to Lol p 5 such as Ph1 p 5 and Poa p 5.

In work leading up to the present invention, the inventors expressed recombinant Lol p 5 in E. coli as a nonfusion protein and found that removal of the N-terminal signal peptide from the cDNA prior to cloning into the bacterial expression vector resulted in a soluble recombinant form of the allergen. This approach made it possible to avoid the harsh denaturing conditions for isolation of the allergen from bacterial cells. Recombinant Lol p 5 was tested for antigenic similarity with its natural counterpart by inhibition ELISA experiments and the inventors showed that the recombinant form fully inhibited IgE binding of an isolated form of its natural pollen counterpart. The fact that single recombinant isoforms can inhibit IgE binding to natural allergens further implied that different allergen isoforms were similar. The inventors used recombinant allergens in immunoblot inhibition studies where allergic sera reincubated with recombinant Lol p 5 were used to probe two dimensional immunoblots of rye-grass soluble protein. It was found in accordance with the present invention that preincubation with one form completely abolished binding to all the different forms encoded by different genes. This showed that even with sequence micro-heterogenities, different allergen isoforms were antigenically very similar.

The next-step in the development of the present invention was to determine key amino acid residues of the allergenic proteins which could be changed which removed or reduced IgE interactivity while maintaining the general structure and functionality of the T-cell epitopes.

The inventors determined which amino acid residues on isoforms A and B of Lol p 5 were conserved. It was reasoned that such conserved amino acid residues would be important for IgE binding since there is cross-reactivity between a number of allergens from different grasses. By selectively mutating these conserved amino acid residues, mutants were identified which have no or reduced IgE interactivity while retaining T-cell antigenicity.

Accordingly, another aspect of the present invention comprises a modified group 5 grass pollen allergen, wherein said group 5 grass pollen allergen comprises a substitution, deletion and/or addition at one or more amino acid residues which is/are conserved in at least two immunologically cross-reactive group 5 grass pollen allergens and wherein said modified group 5 grass pollen allergen lacks or comprises reduced numbers of IgE epitopes and/or exhibits reduced binding capacity for IgE and/or exhibits reduced IgE production-stimulatory activity compared to the corresponding naturally occurring form.

In accordance with the aspect of the present invention, one suitable reference amino acid sequence is SEQ ID NO:1 which is the amino acid sequence of Lol p 5, isoform A. An amino acid sequence comparison, such as in FIG. 1, shows the conserved amino acid residues in isoforms A and B of Lol p 5 and Ph1 p 5 and in isoforms of Poa p 5. Conserved residues in FIG. 1 are indicated by asterisks. Mutants are then readily introduced which alter one or more of these conserved residues.

Another aspect of the present invention provides a modified group 5 grass pollen allergen comprising an amino acid truncation or substitution, deletion and/or addition at a position corresponding to one or more of mutants 1 to 9 of Lol p 5 as depicted in FIG. 3 or a corresponding mutant in an immunologically related allergen.

In a particularly preferred embodiment, the present invention provides a modified Lol p 5 allergen which lacks or comprises a reduced number of IgE epitopes and/or exhibits reduced IgE binding capacity and/or exhibits reduced IgE production-stimulatory activity while retaining T-cell antigenicity wherein said Lol p 5 variant is selected from a molecule having the amino acid sequence set forth in SEQ ID NOs:8 to 12 or a modified allergen corresponding to an immunologically related allergen.

The Lol p 5 variants identified by SEQ ID NOs:8 to 12 are referred to herein as mutants D1 to D5, respectively.

The present invention further provides a nucleic acid molecule comprising a sequence of nucleotides encoding or complementary to a sequence encoding a modified recombinant allergen, wherein said allergen in naturally occurring form is associated with allergic disease conditions in sensitive subjects, wherein said modified recombinant allergen comprises an amino acid sequence modified from the naturally occurring amino acid sequence such that the allergen lacks or comprises reduced numbers of IgE epitopes and/or exhibits reduced binding capacity for IgE and/or exhibits reduced IgE production-stimulatory activity while retaining T-cell antigenicity.

Another aspect of the present invention provides a nucleic acid molecule comprising a sequence of nucleotides encoding or complementary to a sequence encoding a modified recombinant allergen, wherein said allergen in naturally occurring form is associated with type I allergic disease conditions in sensitive subjects, wherein said modified recombinant allergen comprises an amino acid sequence modified from the naturally occurring amino acid sequence such that the allergen lacks or comprises reduced numbers of IgE epitopes and/or exhibits reduced binding capacity for IgE and/or exhibits reduced IgE production-stimulatory activity while retaining T-cell antigenicity.

Yet another aspect of the present invention is directed to a nucleic acid molecule comprising a sequence of nucleotides encoding or complementary to a sequence encoding modified recombinant grass pollen allergen, wherein said grass pollen allergen in naturally occurring form is associated with type I allergic disease conditions in sensitive subjects wherein said modified recombinant grass pollen allergen comprises an amino acid sequence modified from the naturally occurring amino acid sequence such that the allergen lacks or comprises reduced numbers of IgE epitopes and/or exhibits reduced binding capacity for IgE and/or exhibits reduced IgE production-stimulatory activity while retaining T-cell antigenicity.

Still yet another aspect of the present invention relates to a nucleic acid molecule comprising a sequence of nucleotides encoding or complementary to a sequence encoding modified recombinant rye-grass pollen allergen comprising an amino acid sequence modified from the naturally occurring amino acid sequence such that the allergen lacks or comprises reduced numbers of IgE epitopes and/or exhibits reduced binding capacity for IgE and/or exhibits reduced IgE production-stimulatory activity while retaining T-cell antigenicity.

Thus, a particularly preferred aspect of the present invention provides purified nucleic acid molecules encoding a modified grass pollen allergen and more particularly a modified group 5 grass pollen allergen, or an antigenic fragment thereof, or derivative or homolog thereof, or the functional equivalent of such a nucleic acid sequence wherein the modified grass pollen allergen lacks or comprises reduced number of IgE epitopes and/or exhibits reduced binding capacity for IgE and/or exhibits reduced IgE production-stimulatory activity while retaining T-cell antigenicity. Preferred nucleic acid sequences encode group 5 allergen family members such as Lol p 5, Poa p 5 and Ph1 p 5. One particularly useful nucleic acid molecule encodes Lol p 5 mutants D1 to D5.

The nucleic acid molecule of the present invention may be genomic or cDNA molecules or a corresponding mRNA molecule and may be referred to as a gene. Reference to a "gene", in respect of the present invention, means any contiguous sequence of nucleotides, the transcription of which leads to a mRNA molecule or which sequence is a mRNA molecule, which mRNA molecule is capable of being translated into a protein. The gene encoding a group 5 grass pollen allergen family member means the nucleotide sequence encoding the protein or a derivative or a homolog of the protein which may contain single or multiple amino acid substitutions, deletions and/or additions relative to the corresponding naturally occurring molecule. A modified Lol p 5 gene also refers to cDNAs complementary to the mRNAs corresponding to the full or partial length of a Lol p 5 protein having at least one truncated or amino acid substitution, addition and/or deletion relative to the naturally occurring molecules.

The present invention further contemplates fusion molecules. For example, for some aspects of the present invention, it is desirable to produce a fusion protein comprising modified grass pollen allergen or a fragment thereof or a derivative thereof and an amino acid sequence from another peptide or protein, examples of the latter being enzymes such as 1-galactosidase, phosphatase, urease and the like. Most fusion proteins are formed by the expression of a recombinant gene in which two coding sequences have been joined together such that their reading frames are in phase. Alternatively, proteins or peptides can be linked in vitro by chemical means. All such fusion protein or hybrid genetic derivatives of a grass pollen allergen or its encoding nucleotide sequences are encompassed by the present invention. Furthermore, by homologs and derivatives of a grass pollen allergen protein is meant to include synthetic derivatives thereof. The nucleotide sequences as elucidated herein, can be used to chemically synthesize the entire potein or generate any number of fragments (peptides) by chemical synthesis by well known methods (e.g. solid phase synthesis). All such chemically synthesized peptides are encompassed by the present invention. Accordingly, the present invention extends to isolated modified grass pollen allergen family members, fragments thereof and their derivatives, homologs and immunological relatives made by recombinant means or by chemical synthesis.

The terms "isolated" and "purified" are used interchangeably herein and refer to peptides, proteins, protein fragments and nucleic acid sequences substantially free of cellular material or culture medium when produced by recombinant DNA techniques, or chemical precursors or other chemicals when synthesized chemically. The term "naturally occurring" as used herein refers to proteins or fragments thereof purified from grass pollen or other plant part. It also includes reference to an amino acid sequence determined by a cDNA sequence but which is associated with allergic conditions in a similar way to an allergen purified from grass pollen.

Fragments of nucleic acid molecules within the scope of the invention include those coding for parts of grass pollen allergens that exhibit T-cell antigenicity but which lacks or exhibits reduced IgE interaction in mammals, preferably humans.

Fragments and mutants of recombinantly or synthetically produced modified grass pollen allergens which do not bind IgE and/or which have minimal IgE interacting ability and/or which have minimal capacity to stimulate IgE production are desirable. It is preferable that such minimal IgE interacting activity does not lead to histamine release. For example, it is preferable that the modified allergen does not cause cross linking of IgE on mast cells or basophils. Minimal IgE interacting activity refers to IgE interaction activity which is less than the amount of IgE interaction by recombinantly or synthetically produced "naturally occurring" grass pollen allergen protein or whole purified native grass pollen allergen. IgE interaction may also be measured as IgE production stimulating activity. Preferred fragments also include antigenic fragments which, when administered to a grass pollen-sensitive individual or an individual allergic to an allergen cross-reactive with grass pollen allergen, are capable of modifying the allergic response to grass pollen allergen of the individual.

Antigenic fragments of the present invention which have T-cell stimulating activity i.e. T-cell antigenicity, and thus comprise at least one T-cell epitope are particularly desirable. T-cell epitopes are believed to be involved in initiation and perpetuation of the immune response to a protein allergen which is responsible for the clinical symptoms of allergy. These T-cell epitopes are thought to trigger early events at the level of the T helper cell by binding to an appropriate HLA molecule on the surface of an antigen presenting cell and stimulating the relevant T-cell sub-population. These events lead to T-cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokines secreted. A T-cell epitope is the basic element or smallest unit of recognition by a T-cell receptor, where the epitope comprises amino acids essential to receptor recognition. Amino acid sequences which mimic those of the T-cell epitopes and which modify the allergic response to protein allergens are within the scope of this invention.

Exposure of patients to purified modified protein allergens of the present invention or to the antigenic fragments of the present invention which comprise at least one T-cell epitope and are derived from protein allergens may tolerize or anergize appropriate T-cell subpopulations such that they become unresponsive to the protein allergen and do not participate in stimulating an immune response upon such exposure. In addition, administration of the protein allergen of the invention or an antigenic fragment of the present invention which comprises at least one T-cell epitope may modify the lymphokine secretion profile as compared with exposure to the naturally-occurring protein allergen or portion thereof (e.g. result in a decrease of IL-4 and/or an increase in IL-2). Furthermore, exposure to such antigenic fragment or protein allergen may influence T-cell subpopulations which normally participate in the response to the allergen such that these T-cells are drawn away from the site(s) of normal exposure to the allergen (e.g. nasal mucosa, skin and lung) towards the site(s) of therapeutic administration of the fragment or protein allergen. This redistribution of T-cell sub-populations may ameliorate or reduce the ability of an individual's immune system to stimulate the usual immune response at the site of normal exposure to the allergen, resulting in a diminution in allergic symptoms.

The present invention provides expression vectors and host cells transformed to express the nucleic acid sequences of the invention. Expression vectors of the present invention comprise a nucleic acid sequence coding for a modified grass pollen allergen, or an antigenic fragment thereof, or a derivative or homolog thereof, or the functional equivalent of such nucleic acid sequence. The nucleic acid sequences may be expressed in prokaryotic or eukaryotic host cells. Suitable host cells include bacterial cells such as *E. coli*, insect cells, yeast, or mammalian cells such as Chinese hamster ovary cells (CHO). Suitable expression vectors, promoters, enhancers, and other expression control elements may be found in Sambrook et al., *Molecular Cloning: A Laboratory Manual*, second edition, Cold Spring Harbor Laboratory Press, Cold Spring Harbor, N.Y., 1989. Suitable vectors for expression in yeast include YepSec1 (Baldari et al., *EMBO J.* 6: 229-234, 1987); pMF (Kurjan and Herskowtiz, *Cell* 30: 933-943, 1982); and JRY88 (Schultz et al., *Gene* 54: 113-123, 1987).

Host cells can be transformed to express the nucleic acid sequences of the present invention using conventional techniques such as calcium phosphate or calcium chloride co-precipitation, DEAE-dextran-mediated transfection, or electroporation. Suitable methods for transforming the host cells may be found in Sambrook et al., 1989, supra, and other laboratory textbooks. The nucleic acid sequences of the invention may also be synthesized using standard techniques.

Accordingly, another aspect of the present invention provides a method of producing a recombinant modified grass allergen or a fragment thereof, or a derivative or homolog thereof, or immunological relatives thereof comprising culturing an organism containing a replicable recombinant DNA molecule, said molecule comprising a promoter capable of expression in said organism, a gene encoding a modified grass pollen allergen or family member, a fragment or homolog or derivative thereof, or an immunological relative thereof, located downstream of and transcribed from said promoter, a selectable marker and a DNA vehicle containing a prokaryotic or eukaryotic origin of replication, under conditions and for a time sufficient for said recombinant DNA molecule to be stably maintained and direct the synthesis of the modified grass pollen allergen or fragment or derivative, homolog or immunological relative thereof and then optionally isolating same.

The grass pollen allergens and fragments (peptides) thereof can be purified from cell culture medium, host cells, or both using techniques known in the art for purifying peptides and proteins, including ion-exchange chromatography, gel filtration chromatography, ultrafiltration, electrophoresis and immunopurification with antibodies specific for the modified grass pollen allergen. The terms "isolated" and "purified" are used interchangeably herein and refer to peptides, proteins, protein fragments, and nucleic acid sequences substantially free of cellular material or culture medium when produced by recombinant DNA techniques, or chemical precursors or other chemicals when synthesized chemically.

Another aspect of the invention provides protein preparations comprising Lol p5 D1, D2, D3, D4 and D5 or their functional or immunological equivalents, homologs or derivatives.

Thus, the present invention provides modified grass pollen allergens or their derivatives which, when administered to a grass pollen-sensitive individual, reduce the allergic response of the individual to grass pollen such as rye-grass pollen or pollen from immunologically related grasses. Preferred modified grass pollen allergens include modified Lol p5 protein or a derivative or homolog thereof. Other preferred allergens are Phl p 5 and Poa p 5.

In addition to inducing an amino substitution, addition and/or deletion or truncation, another example of a modification of proteins or peptides is substitution of cysteine residues preferably with alanine, serine, threonine, leucine or glutamic acid to minimize dimerization via disulfide linkages. Another example of modification of the proteins and peptides of the invention is by chemical modification of amino acid side chains or cyclization of the peptide.

In order to enhance stability and/or reactivity, proteins or peptides of the invention can also be modified to incorporate one or more polymorphisms in the amino acid sequence of the protein allergen resulting from natural allelic variation. Additionally, D-amino acids, non-natural amino acids or non-amino acid analogs can be substituted or added to produce a modified protein or peptide within the scope of this invention.

Another aspect of the present invention relates to recombinant vectors comprising DNA sequences encoding proteins displaying modified allergenic activity from pollen of a grass species. More particularly, the grass species belongs to the family Poaceae (Gramineae), and even more particularly, to the genus *Lolium*. Still even more particularly, the allergenic protein is characterized as being immunologically cross-reactive with antibody to Lol pIb protein of *Lolium perenne* pollen, namely:

Pooid (festucoid) grasses. Group 1: Triticanea: *Bromus inermis*, smooth broom; *Agropyron repens*, English couch; *A. cristatum; Secale cereale* rye *Triticum aestivum* wheat. Group 2: Poanae: *Dactylis glomerata*, orchard grass of perennial ryegrass; *L. multiflorum*, Italian ryegrass; *Poa pratensis*, Kentucky bluegrass; *P. compressa*, flattened meadow grass; *Avena sativa*, oat; *Holcus lanatus*, velvet grass or Yorkshire fog; *Anthoxanthum odoratum*; sweet vernal grass; *Arrhenatherum elatius*, oat grass; *Agrostis alba*, red top; *Phleum pratense*, timothy; *Phalaris arundinacea*, reed canary grass. Panicoid grass, *Paspalum notatum*, Bahia grass, Andropogonoid grasses: *Sorghum halepensis*, Johnson grass.

A variety of expression vectors can be constructed for the production of a modified grass pollen allergen or a fragment or derivative thereof.

The present invention extends to monoclonal and polyclonal antibodies to modified grass pollen allergens or fragments, derivatives or homologs thereof.

The monoclonal antibodies are useful to screen cDNA libraries or to purified recombinantly produced proteins or even in therapy to reduce the activity of an introduced protein. In the following discussion, reference to grass pollen protein allergens include their derivatives, homologs and immunological relatives and chemical synthetic derivatives thereof. The following discussion also includes antibodies specific for purified modified Lol p 5 and fragments, derivatives and homologs thereof. Such antibodies are contemplated to be useful in developing detection assays (immunoassays) for modified grass pollen allergens especially during the monitoring of a therapeutic or diagnostic regimen and in the purification of recombinantly or synthetically produced grass pollen family members and in particular group 5 grass pollen allergen. The antibodies may be monoclonal or polyclonal. Additionally, it is within the scope of this invention to include any second antibodies (monoclonal or polyclonal) directed to the first antibodies discussed above. The present invention further contemplates use of these first or second antibodies in detection assays and, for example, in monitoring the effect of a diagnostic or an administered pharmaceutical preparation. Furthermore, it is within the scope of the present invention to include antibodies to any molecules complexed with a modified grass pollen protein allergen. Accordingly, an antibody to a grass pollen protein allergen encompasses antibodies to such a protein allergen, or antigenic parts thereof, and to any associated molecules (e.g. lipid regions, carrier molecules, fused proteins, and the like).

The grass pollen family members, or fragments thereof, considered herein are purified then utilized in antibody production. Both polyclonal and monoclonal antibodies are obtainable by immunization with recombinant or synthetic modified grass pollen protein family members, and either type is utilizable for immunoassays. The methods of obtaining both types of sera are well known in the art. Polyclonal sera are less preferred but are relatively easily prepared by injection of a suitable laboratory animal with an effective amount of a purified modified grass pollen allergen, or antigenic parts thereof, collecting serum from the animal, and isolating specific sera by any of the known immunoabsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Kohler and Milstein, *Nature* 256: 495-499, 1975; Kohler and Milsten, *Eur. J. Immunol* 6: 511-519, 1976).

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or non-human) cell lines are available. For the purpose of the present invention, the animal of choice may be injected with from about 0.1 mg to about 20 mg of purified modified grass pollen allergen or parts thereof. Usually the injecting material is emulsified in Freund's complete adjuvant. Boosting injections may also be required. The detection of antibody production can be carried out by testing the antisera with appropriately labeled antigen. Lymphocytes can be obtained by removing the spleen or lymph nodes of sensitized animals in a sterile fashion and carrying out fusion. Alternatively, lymphocytes can be stimulated or immunized in vitro.

The presence of modified grass pollen allergens contemplated herein, or antibodies specific for same, in a patient's serum, plant or mammalian tissue or tissue extract, can be detected utilizing antibodies prepared as above, either monoclonal or polyclonal, in virtually any type of immunoassay. A wide range of immunoassay techniques are available as can be seen by reference to U.S. Pat. Nos. 4,015,043, 4,424,279 and 4,018,653. This includes both single-site and two-site, or "sandwich", assays of the non-competitive types, as well as in the traditional competitive binding assays. Sandwich assays are among the most useful and commonly used assays and are favored for use in the present invention. A number of variations of the sandwich assay technique exist, and all are intended to be encompassed by the present invention. Briefly, in a typical forward assay, an unlabeled antibody is immobilized in a solid substrate and the sample to be tested brought into contact with the bound molecule. After a suitable period of incubation, for a period of time sufficient to allow formation of an antibody-antigen secondary complex, a second antibody, labeled with a reporter molecule capable of producing a detectable signal is then added and incubated, allowing time sufficient for the formation of a tertiary complex of antibody-antigen-labeled antibody (e.g., antibody-modified grass pollen allergen protein-antibody). Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody, or a reverse assay in which the labeled antibody and sample to be tested are first combined, incubated and then added simultaneously to the bound antibody. These techniques are well known to those skilled in the art, including any minor variations as will be readily apparent.

Although the following discussion is concerned with detecting modified grass pollen allergen, it is equally applicable to detecting antibodies to same and it is intended to be a sufficient description thereof.

In the typical forward sandwich assay a first antibody having specificity for modified grass pollen allergen, or antigenic parts thereof, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated from about room temperature to about 37° C. for a period of time sufficient to allow binding of any subunit present in the antibody. The incubation period will vary but will generally be in the range of about 2-40 minutes or overnight if more convenient. Following the incubation period, the antibody subunit solid phase is washed and dried and incubated with a second antibody specific for a portion of the hapten. The second antibody is linked to a reporter molecule which is used to indicate the binding of the second antibody to the hapten.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates, for peroxidase conjugates, 1,2-phenylenediamine, 5-aminosalicylic acid, or toluidine are commonly used. It is also possible to employ fluorogenic substrates, which yield a fluorescent product rather than the chromogenic substrates noted above. In all cases, the enzyme-labeled antibody is added to the first antibody hapten complex, allowed to bind, and then the excess reagent is washed away. A solution containing the appropriate substrate is then added to the tertiary complex of antibody-antigen-antibody. The substrate will react with the enzyme linked to the second antibody, giving a qualitative visual signal, which may be further quantitated, usually spectophotometrically, to give an indication of the amount of hapten which was present in the sample. "Reporter molecule" also extends to use of cell agglutination or inhibition of agglutination such as red blood cells or latex beads, and the like.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state of excitability in the molecule, followed by emission of the light at a characteristic color visually detectable with a light microscope. As in the EIA, the fluorescent labeled antibody is allowed to bind to the first antibody-hapten complex. After washing off the unbound reagent, the remaining tertiary complex is then exposed to the light of the appropriate wavelength, the fluorescein observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose. It will also be apparent that the foregoing can be used to detect directly or indirectly (i.e. via antibodies) grass pollen allergen protein of this invention.

Accordingly, one aspect of the present invention provides a method of detecting a modified pollen allergen or a derivative or homolog thereof or an allergenic protein immunologically reactive with said modified grass pollen allergen or a derivative or homolog present in serum, tissue extract, plant extract or other biological fluid or composition comprising the steps of containing said fluid or composition to be tested with an antibody to said modified grass pollen protein allergen for a time and under conditions sufficient for a modified allergenic protein-antibody complex to form and subjecting said complex to a detecting means. For purification methods, an antibody to a native allergen may also be effective in order to purify a modified allergen and such an embodiment is encompassed by the present invention.

The present invention is also directed to a kit for the rapid and convenient assay for antibodies to modified grass pollen allergens or derivatives, homologs or immunological relatives thereof in mammalian body fluids e.g. serum, tissue extracts, tissue fluids), in vitro cell culture supernatants, and cell lysates. The kit is compartmentalized to receive a first container adapted to contain an antigenic component thereof, and a second container adapted to contain an antibody to the grass pollen allergen, said antibody being labeled with a reporter molecule capable of giving a detectable signal. If the reporter molecule is an enzyme, then a third container adapted to contain a substrate for said enzyme is provided. In an exemplified use of the subject kit, a sample to be tested is contacted with the contents of the first container for a time and under conditions for an antibody, if present in the sample, to bind to the grass pollen allergen in said first container.

Because of the presence of allergens in the environment, hayfever and seasonal asthma continue to have significant morbidity and socio-economic impact on Western communities, despite advances made in their pharmacology and immunology. While the available spectrum of drugs, including antihistamines and steroids have resulted in improvement in the treatment of allergic disease, they have unfortunate side-effects associated with long term usage. Because of these problems, renewed interest has been shown in the immunotherapy of allergic disease. Immunotherapy involves the injection of potent allergen extracts to desensitize patients against allergic reactions. Unfortunately, the pollen preparations used as allergens are polyvalent and of poor quality. Consequently, concentrations used are frequently high in order to induce IgG responses, but may be lethal through triggering of systemic reactions, including anaphylaxis. The cloned gene product or synthetic peptides based on the sequence of allergens provides a safer medium for Therapy since it can be quality controlled, characterized and standardized.

Accordingly, the present invention contemplates a method for desensitizing a mammal (e.g. human) allergic to grass pollen which comprises administering to said mammal a desensitizing-effective amount of a modified grass pollen allergen which lacks or comprises reduced numbers of and/or exhibits reduced IgE binding activity and/or exhibits reduced IgE production-stimulatory activity or a fragment or derivative, homolog, or immunological relative thereof, for a time and under conditions sufficient to effect desensitization of the mammal (e.g. human) to the grass pollen.

The present invention also provides a method of treating sensitivity to ryegrass pollen or pollen from an immunological relative of rye-grass in a mammal (e.g. human) sensitive to such pollen, comprising administering to the mammal a therapeutically effective amount of a therapeutic composition of the invention. The present invention further provides a method of treating sensitivity to ryegrass pollen allergen or an allergen immunologically cross-reactive with ryegrass pollen allergen comprising administering to a mammal a therapeutically effective amount of said protein preparation of the invention.

Through the use of the peptides and protein of the present invention, preparations of consistent, well-defined composition and biological activity can be made and administered for therapeutic purposes (e.g. to modify the allergic response of a *L. perenne* sensitive individual to pollen of such plant. Administration of such peptides or protein may, for example, modify IgE response to the grass pollen allergen. Purified peptides can also be used to study the mechanism of immunotherapy of *L. perenne* allergy and to design modified derivatives or analogs useful in immunotherapy.

The present invention is directed, therefore, to the use of a modified allergen in the manufacture of a medicament for the treatment or prophylaxis of allergen-sensitive individuals.

The present invention, therefore, provides a pharmaceutical composition comprising a desensitizing or therapeutically effective amount of modified grass pollen allergen and in particular group 5 grass pollen allergen or derivatives, homologs or immunological relatives thereof and one or more pharmaceutically acceptable carriers and/or diluents. The active ingredients of a pharmaceutical composition comprising the modified grass pollen allergen prophylactic is contemplated to exhibit excellent therapeutic or activity, for example, in the desensitization of humans allergic to grass pollen when administered in amount which depends on the particular case. For example, from about 0.5 Fg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The activity compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredients which comprise the pharmaceutical composition of the invention may be required to be coated in a material to protect said ingredients from the action of enzymes, acids and other natural conditions which may inactivate said ingredients. For example, the modified grass pollen allergen may be administered in an adjuvant, co-administered with enzyme inhibitors or in liposomes. Adjuvant is used in its broadest sense and includes any immune stimulating compound, such as interferon. Adjuvants contemplated herein include resorcinols, non-ionic surfactants such as polyoxyethylene oleyl ether and n-hexadecyl polyethylene ether. Enzyme inhibitors include pancreatic trypsin. Liposomes include water-in-oil-in-water CF emulsions as well as conventional liposomes. For purposes of inducing T cell anergy, the pharmaceutical composition if preferably administered in non-immunogenic form (e.g. it does not contain adjuvant).

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions or sterile powders for preparation of injectable solutions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, iropylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When a modified grass pollen allergen, or a fragment thereof is suitably protected as described above, the active compound may be orally administered, for example, with an inert diluent or with an assimilable edible carrier, or it may be enclosed in hard or soft shell gelatin capsule, or it may be compressed into tablets or it may be incorporated directly with food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be carried and may conveniently be between about 5 to 80% of the weight of the unit. The amount of active compound in such therapeutically useful compositions is such that a suitable dosage will be obtained. Preferred compositions or preparations according to the present invention are prepared so that an oral dosage unit form contains between about 10 Fg and 2000 mg of active compound.

The tablets, troches, pills, capsules and the like may also contain the ingredients listed below: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and prppylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The present invention is further described by the following non-limiting Examples.

EXAMPLE 1

Generation of Lol p 5 Mutant Proteins

To engineer hypoallergenic, non-IgE reactive allergen variants, it was required to be determined whether key residues of the proteins can be selected which can be changed while keeping the general structure and T-cell epitopes intact. Since the highest frequency of IgE binding is observed in peptide fragments which span the C-terminal half of Lol p 5, the inventors introduced mutations predominantly in the C-terminus of the allergen. To identify amino acid positions in Lol p 5 likely to have an influence on the IgE interactivity of the protein, protein sequences of isoform A and B of Lol p 5 were compared with group 5 allergens of other grasses (FIG. 1). Site-directed mutagenesis was employed to replace residues that are highly conserved among group 5 allergens (FIG. 2). Mutant proteins altered in one or three domains were generated (FIG. 3).

Figure 5:
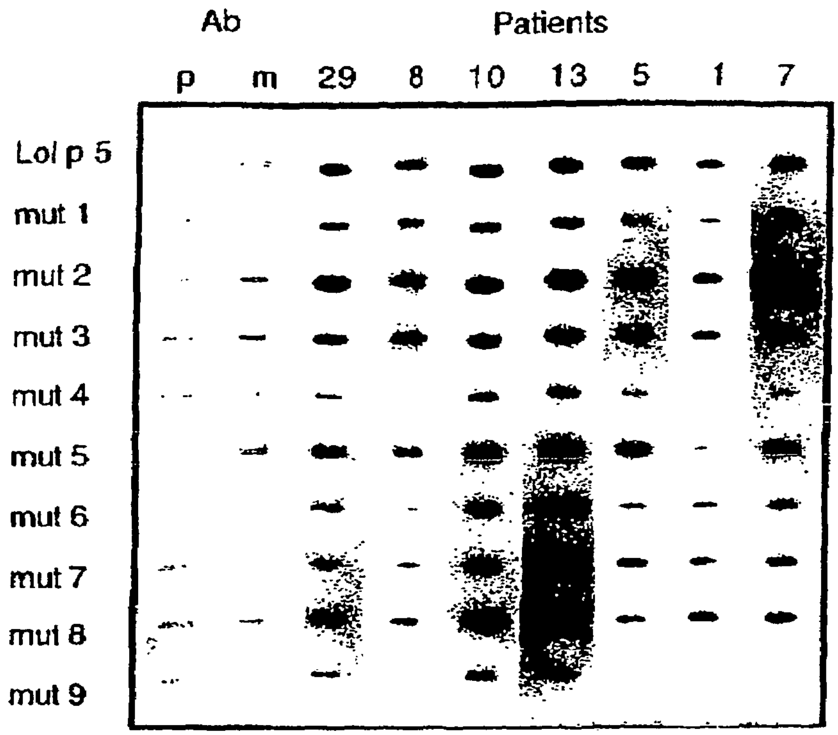
FIG. 5 is a diagrammatic representation showing slot blot analysis of Lol p 5 (non-mutated) and the nine mutated variants (mut 1 to mut 9) of reactivities of the purified proteins to a polyclonal (p), a monoclonal (m) antibody and to sera of 7 rye-grass pollen-allergic patients.
Figure 6:
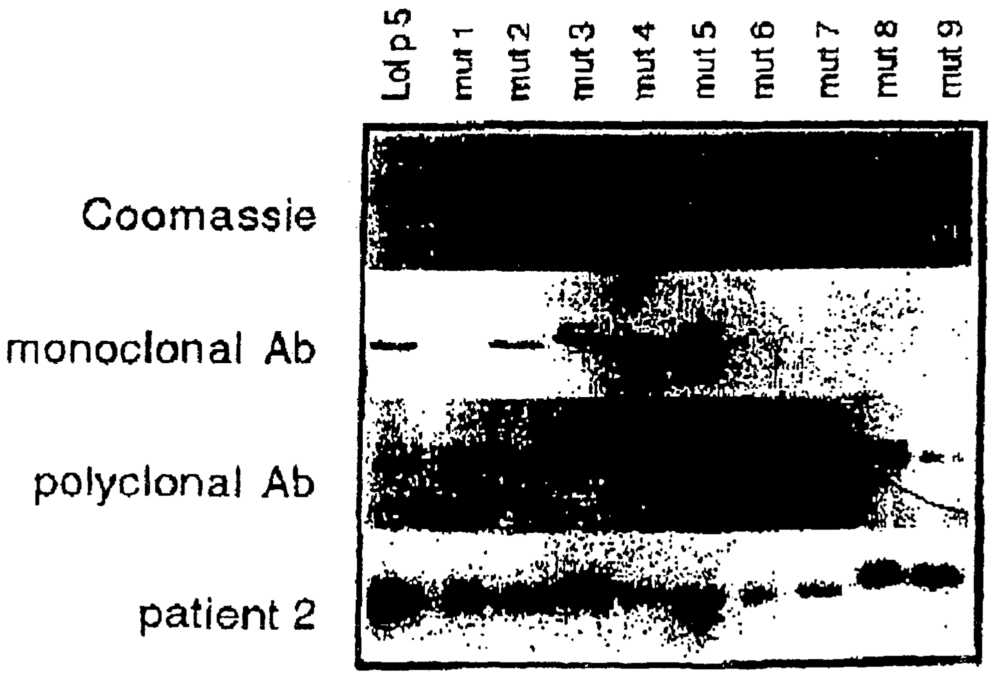
FIG. 6 is a diagrammatic representation showing immunoblot analyses of Lol p 5 (non-mutated) and the nine mutated variants (mut 1 to mut 9) of reactivities of the purified proteins to a polyclonal (p), a monoclonal (m) antibody and to the serum of a rye-grass pollen-allergic patient (patient 2).
Figure 7A:
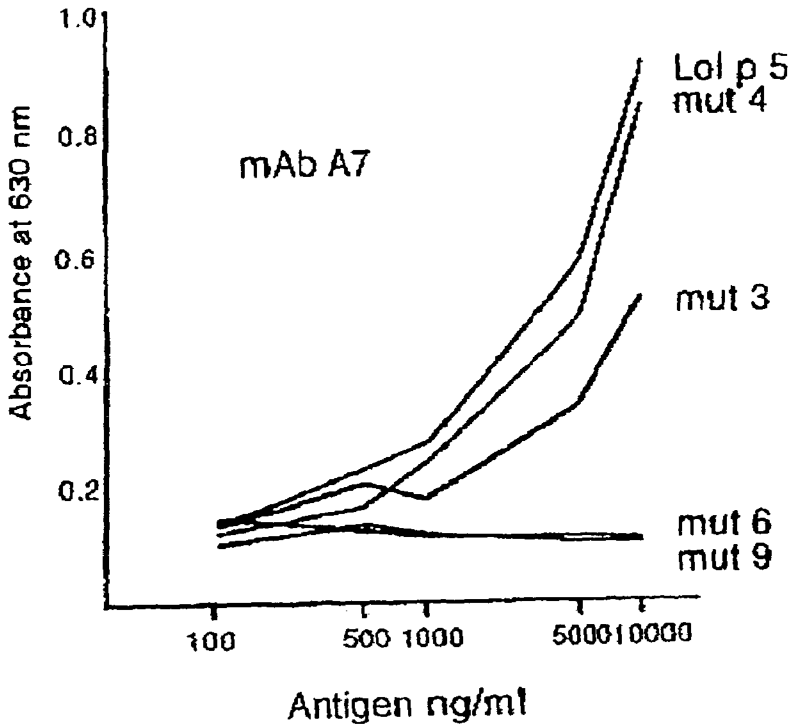
FIGS. 7A, B and C are graphical representations of ELISA assays using purified non-mutated Lol p 5 and four of the mutated proteins (mut 3, mut 4, mut 6, mut 9) showing a reduction in reactivity of the mutated variants to a monoclonal (mAb A7) and to IgE of two patients (patient 4, patient 27).
Figure 7B:
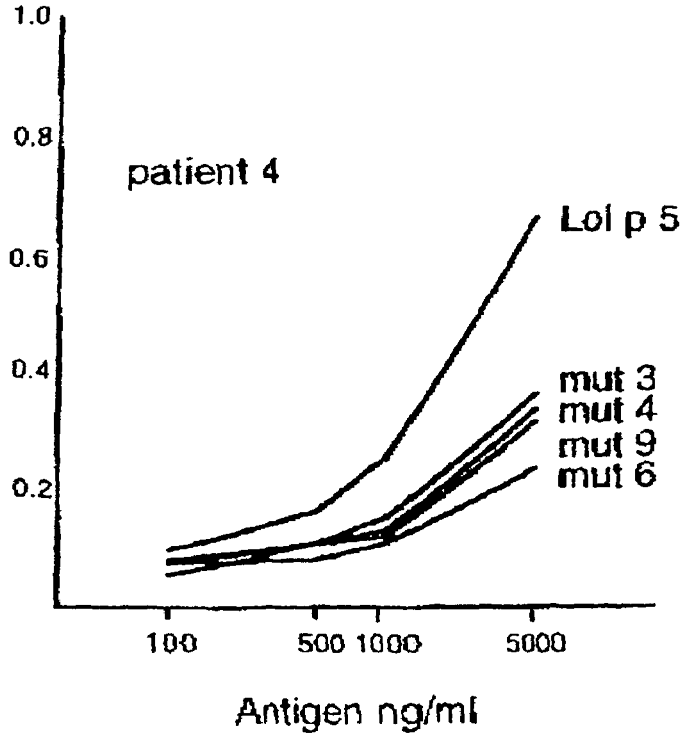
Figure 7C:
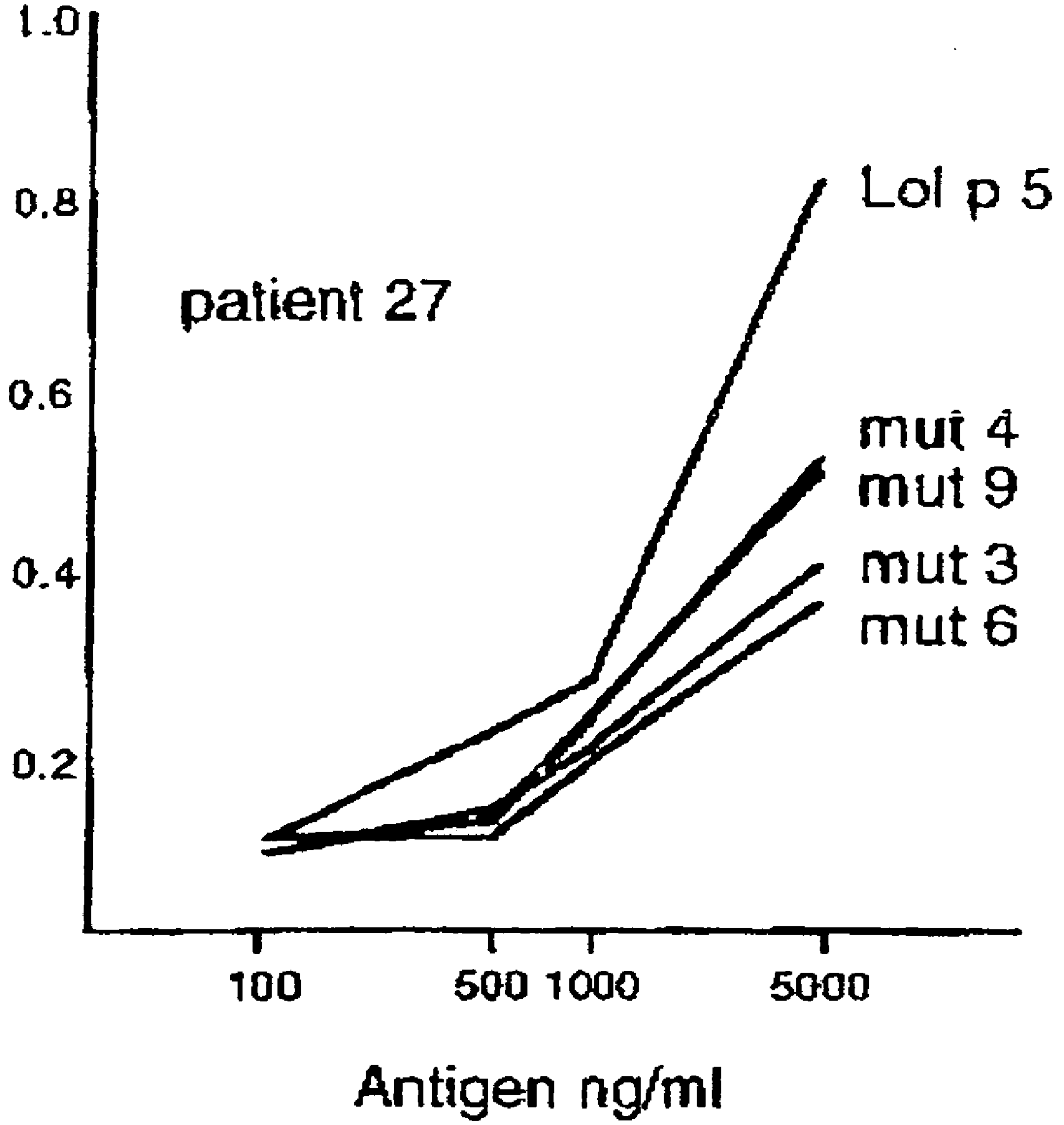

Non-mutated Lol p 5 and mutated variants of Lol p 5 were expressed in soluble forms in *E. coli* using the pQE expression vector system (Qiagen). Bacterial expression (see below) of proteins using this vector introduces a polyhistidine tag at the N-terminus of the molecules which is useful for purification of recombinant proteins by one step metal chelate affinity chromatography. Non-mutagenized control and mutated proteins were then tested for IgE reactivity as well as for reactivity with anti-Lol p 5 monoclonal antibody A7 (Mab A7) and polyclonal anti-Lol p 5 antiserum in slot blots (FIG. 5), Western blots (FIG. 6) and ELISA assays (FIG. 7). The results showed a substantial reduction in IgE binding activity in case of several of the mutated proteins (e.g. mut 4, mut 6, mut 9). Such engineered allergenic molecules are potentially useful for safer and more effective immunotherapy for type I allergic diseases and the described approach may be generally applied to produce non-IgE reactive variants of allergens.

EXAMPLE 2

Expression and Purification of Recombinant Lol P 5 and Mutant Proteins

The coding sequences of Lol p 5 and the mutant proteins were introduced in-frame into the expression vector pQE31 (QIAGEN). The vector allows expression of recombinant proteins with an N-terminal, 6-residue histidine tag. Expression and harvesting of the proteins was carried out as outlined in the QIA expressionist manual. Histidine-tagged proteins were purified using TALON metal affinity resin (Clontech), following the procedure for batch/gravity flow column purification as outlined in the TALON Metal Affinity Resin user manual (Clontech).

EXAMPLE 3

SDS-Page and Western Blotting

For SDS-PAGE, 1.3 Fg of Lol p5 and each of the mutant proteins were boiled for 5 minutes with 10× protein sample buffer. Samples were loaded onto a 15% w/v acrylamide mini gel at 200 V for 40 minutes in a buffer of 0.2 M glycine, 0.025 M Tris, 0.1% w/v SDS.

For staining, gels were shaken in 0.1% w/v Coomassie Brilliant Blue R250 for at least an hour. Gels were destained in 20% v/v methanol, 7% v/v glacial acetic acid, 3% v/v glycerol, overnight with two buffer changes.

Gels were western blotted in a BIORAD mini-Protean II cell western blot apparatus in a buffer of 0.025 M Tris, 0.2 M glycine, 20% v/v methanol onto Nytran 0.2 Fm nylon membrane (Schleicher & Schuell) at 100 V for 1 hour at 4° C.

EXAMPLE 4

Slot Blot Analysis

For slot blot analysis, 0.7 Fg of mutant proteins and Lol p5 were added into the slots of a Hybri-Slot manifold slot blot apparatus (Life Technologies, Inc.) and blotted onto Nytran 0.2 Fm nylon membrane (Schleicher & Schuell) under suction from a water vacuum.

EXAMPLE 5

Incubation of Blots with Antibodies and Patient Sera

Prior to incubation with antibodies or sera, all western and slot blots were blocked in 10% w/v skim milk powder in PBS (150 mM sodium chloride, 36 mM sodium phosphate monobasic, monohydrate, 7 mM sodium phosphate dibasic, dihydrate) for one hour with shaking. Blots were washed once with PBS, 0.5% v/v Tween 20, twice with PBS and incubated overnight with monoclonal antibodies (mAb A7: diluted 1:5), polyclonal antibodies (B1: diluted 1:50) or patient sera. All dilutions were prepared in PBS, 0.5% w/v BSA, 0.1% w/v sodium azide, and shaken with the blots overnight at room temperature. After washing as above blots were incubated with alkaline-phosphatase conjugated anti-mouse (mAb A7) or anti-rabbit (B1) secondary antibodies (Promega) diluted 1:5000 in PBS, 0.5% v/v Tween 20, 1% w/v BSA for 1 hour with shaking at room temperature. All blots were than washed as above. Bound anti-mouse and anti-rabbit antibodies were detected by a colour reaction—10 ml alkaline phosphatase buffer (0.1 M Tris, pH 9.5, 0.1 M sodium chloride, 0.05 M magnesium chloride) with 66 Fl of BCIP stock (5% w/v bromochloroindolyl phosphate in 100% v/v dimethylfomamide). Blots incubated with patient sera were probed with $I^{125}$-labeled anti-human antibody (Bioclone) diluted 1:5 in PBS, 0.5% v/v Tween 20, 1% w/v BSA (buffer B) overnight with shaking at room temperature. All blots were washed as above. After washing, bound $I^{125}$-labeled anti-human IgE was detectd by exposure to Kodak Biomax MS film at −70° C.

EXAMPLE 6

Direct ELISA

The wells of an ELISA plate (Greiner) were coated with 50 Fl aliquots of 100, 500, 1000, 5000 and 10000 ng/ml dilutions of Lol p5 and the four mutant proteins, and incubated at 4° C. overnight. The wells were then washed four times with PBS, 0.5% v/v Tween 20. After blocking with buffer B at room temperature for one hour, the wells were washed again, and incubated with 50 Fl of an appropriate dilution of patient sera in buffer B at 4° C. overnight. Wells were washed as above before incubation with 50 Fl of a 1:2000 dilution of anti-human IgE antibody (Alkaline-Phosphatase conjugated: Sigma) in buffer B at room temperature for one hour. After a final series of washes, bound anti-human IgE was detected with Blue Phos microwell phosphatase substrate system (Kirkegaard & Perry Laboratories). Colour development was detected by a Spectracount plate reader at 630 m (Packard).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Bond, J. F, Segal, D. B, Yu X-B, Theriault, K. A, Pollock, M. S, Yeung H. *J. Allergy Clin. Immunol.* 91: 339, 1993.

Baldari et al, *EMBO J.* 6: 229-234, 1989.

Kohler and Milstein, *Nature* 256: 495-499, 1975.

Kohler and Milstein, *Eur. J. Immunol.* 6: 511-519, 1976.

Kurjan and Herskowitz, *Cell* 30: 933-943, 1982.

Miyamoto T: Advances in Allergology and Clinical Immunology. Godard P, Bousquet J, Michel FB (eds) pp. 343-347. The Parthenon Publishing Group, Cornforth, UK, 1992.

Ong, E. K, Griffith, I. J., Knox, R. B., Singh, M. B. *Gene* 134: 235-240, 1993.

Sambrook et al., *Molecular Cloning: A Laboratory Manual,* $2^{nd}$ Ed. Cold Spring Harbor Laboratory Press, Cold Spring Harbor, N.Y., 1989.

Schultz et al, *Gene* 54: 113-123, 1987.

Singh, M. B., Hough, T., Theerakulpisut, P., Avjioglu, A., Davies, S., Smith, P. M., Taylor, P., Simpson, R. J., Ward. L. D., McCluskey, J., Puy, R., Knox, R. B. *Proc. Natl. Acad. Sci USA* 88: 13841388, 1991.

Smart, I. J., Heddle, R. J., Zola, H., Bradley, J., *Int. Arch. Allergy Immunol.* 72: 243-248, 1983.

Smith, P. M., Ong, E. K, Avjioglu, A., Singh, M. B., Knox, R. B. Analysis of rye-grass pollen allergens using two dimensional electrophoresis and immunoblotting. In Kraft D (ed), Molecular Biology and Immunology of Allergens, CRC Press, Boca Raton, Fla., 1993.

Smith, P. M., Ong, E. K., Knox, R. B., Singh, M. B. *Mol. Immunol.* 31: 491-498, 1994.

Wuthrich, B., *Int. Arch. Allergy Immunol.* 90: 3-10, 1989.

The invention claimed is:

1. An isolated protein allergen variant, comprising the amino acid sequence set forth in SEQ ID NO: 11 or SEQ ID NO: 12.

2. An isolated Lol p 5 protein allergen variant, comprising the amino acid sequence set forth in SEQ ID NO: 1 with mutations K172N, F173L, T174A and V175A or mutations A204G, V205A and K206A.

3. An isolated Lol p 5 protein allergen variant, comprising the amino acid sequence set forth in SEQ ID NO: 2 with mutations Ki 90N, Fl 91L, TI 92A and V193A or mutations A222G, V223A and K224A.

* * * * *

UNITED STATES PATENT AND TRADEMARK OFFICE

CERTIFICATE OF CORRECTION

PATENT NO. : 7,666,428 B2
APPLICATION NO. : 10/490305
DATED : February 23, 2010
INVENTOR(S) : Deweerd et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 740 days.

Signed and Sealed this

Twenty-eighth Day of December, 2010

David J. Kappos
*Director of the United States Patent and Trademark Office*

SEQUENCE LISTING

```
<160> NUMBER OF SEQ ID NOS: 22

<210> SEQ ID NO 1
<211> LENGTH: 276
<212> TYPE: PRT
<213> ORGANISM: Lolium perenne

<400> SEQUENCE: 1

Ala Asp Ala Gly Tyr Thr Pro Ala Ala Ala Ala Thr Pro Ala Thr Pro
 1               5                  10                  15

Ala Ala Thr Pro Ala Ala Ala Gly Gly Lys Ala Thr Thr Asp Glu Gln
            20                  25                  30

Lys Leu Leu Glu Asp Val Asn Ala Gly Phe Lys Ala Ala Val Ala Ala
        35                  40                  45

Ala Ala Asn Ala Pro Pro Ala Asp Lys Phe Lys Ile Phe Glu Ala Ala
    50                  55                  60

Phe Ser Glu Ser Ser Lys Gly Leu Leu Ala Thr Ser Ala Ala Lys Ala
```

-continued

```
 65                  70                  75                  80

Pro Gly Leu Ile Pro Lys Leu Asp Thr Ala Tyr Asp Val Ala Tyr Lys
                 85                  90                  95

Ala Ala Glu Gly Ala Thr Pro Glu Ala Lys Tyr Asp Ala Phe Val Thr
            100                 105                 110

Ala Leu Thr Glu Ala Leu Arg Val Ile Ala Gly Ala Leu Glu Val His
        115                 120                 125

Ala Val Lys Pro Ala Thr Glu Glu Val Pro Ala Ala Lys Ile Pro Thr
    130                 135                 140

Gly Glu Leu Gln Ile Val Asp Lys Ile Asp Ala Ala Phe Lys Ile Ala
145                 150                 155                 160

Ala Thr Ala Ala Asn Ala Ala Pro Thr Asn Asp Lys Phe Thr Val Phe
                165                 170                 175

Glu Ser Ala Phe Asn Lys Ala Leu Asn Glu Cys Thr Gly Gly Ala Tyr
            180                 185                 190

Glu Thr Tyr Lys Phe Ile Pro Ser Leu Glu Ala Ala Val Lys Gln Ala
        195                 200                 205

Tyr Ala Ala Thr Val Ala Ala Ala Pro Glu Val Lys Tyr Ala Val Phe
    210                 215                 220

Glu Ala Ala Leu Thr Lys Ala Ile Thr Ala Met Thr Gln Ala Gln Lys
225                 230                 235                 240

Ala Gly Lys Pro Ala Ala Ala Ala Ala Thr Gly Ala Ala Thr Val Ala
                245                 250                 255

Thr Gly Ala Ala Thr Ala Ala Ala Gly Ala Ala Thr Ala Ala Ala Gly
            260                 265                 270

Gly Tyr Lys Ala
        275


<210> SEQ ID NO 2
<211> LENGTH: 314
<212> TYPE: PRT
<213> ORGANISM: Lolium perenne

<400> SEQUENCE: 2

Ala Asp Ala Gly Tyr Ala Pro Ala Thr Pro Ala Thr Pro Ala Ala Pro
  1               5                  10                  15

Ala Thr Ala Ala Thr Pro Ala Thr Pro Ala Thr Pro Ala Thr Pro Ala
             20                  25                  30

Ala Val Pro Ser Gly Lys Ala Thr Thr Glu Glu Gln Lys Leu Ile Glu
         35                  40                  45

Lys Ile Asn Ala Gly Phe Lys Ala Ala Val Ala Ala Ala Ala Val Val
     50                  55                  60

Pro Pro Ala Asp Lys Tyr Lys Thr Phe Val Glu Thr Phe Gly Thr Ala
 65                  70                  75                  80

Thr Asn Lys Ala Phe Val Glu Gly Leu Ala Ser Gly Tyr Ala Asp Gln
                 85                  90                  95

Ser Lys Asn Gln Leu Thr Ser Lys Leu Asp Ala Ala Leu Lys Leu Ala
            100                 105                 110

Tyr Glu Ala Ala Gln Gly Ala Thr Pro Glu Ala Lys Tyr Asp Ala Tyr
        115                 120                 125

Val Ala Thr Leu Thr Glu Ala Leu Arg Val Ile Ala Gly Thr Leu Glu
    130                 135                 140

Val His Ala Val Lys Pro Ala Ala Glu Glu Val Lys Val Gly Ala Ile
145                 150                 155                 160
```

-continued

```
Pro Ala Ala Glu Val Gln Leu Ile Asp Lys Val Asp Ala Ala Tyr Arg
                165                 170                 175

Thr Ala Ala Thr Ala Ala Asn Ala Ala Pro Ala Asn Asp Lys Phe Thr
            180                 185                 190

Val Phe Glu Asn Thr Phe Asn Asn Ala Ile Lys Val Ser Leu Gly Ala
        195                 200                 205

Ala Tyr Asp Ser Tyr Lys Phe Ile Pro Thr Leu Val Ala Ala Val Lys
    210                 215                 220

Gln Ala Tyr Ala Ala Lys Gln Ala Thr Ala Pro Glu Val Lys Tyr Thr
225                 230                 235                 240

Val Ser Glu Thr Ala Leu Lys Lys Ala Val Thr Ala Met Ser Glu Ala
                245                 250                 255

Glu Lys Glu Ala Thr Pro Ala Ala Ala Ala Thr Ala Thr Pro Thr Pro
            260                 265                 270

Ala Ala Ala Thr Ala Thr Ala Thr Pro Ala Ala Ala Tyr Ala Thr Ala
        275                 280                 285

Thr Pro Ala Ala Ala Thr Gly Thr Ala Thr Pro Ala Ala Ala Thr Ala
    290                 295                 300

Thr Pro Ala Ala Ala Gly Gly Tyr Lys Val
305                 310


<210> SEQ ID NO 3
<211> LENGTH: 285
<212> TYPE: PRT
<213> ORGANISM: Phleum pratense

<400> SEQUENCE: 3

Ala Asp Leu Gly Tyr Gly Pro Ala Thr Pro Ala Pro Ala Ala Gly Tyr
  1               5                  10                  15

Thr Pro Ala Thr Pro Ala Ala Pro Ala Gly Ala Asp Ala Ala Gly Lys
             20                  25                  30

Ala Thr Thr Glu Glu Gln Lys Leu Ile Glu Lys Ile Asn Ala Gly Phe
         35                  40                  45

Lys Ala Ala Leu Ala Gly Ala Gly Val Gln Pro Pro Ala Asp Lys Tyr
     50                  55                  60

Arg Thr Phe Val Ala Thr Phe Gly Pro Ala Ser Asn Lys Ala Phe Ala
 65                  70                  75                  80

Glu Gly Leu Ser Gly Glu Pro Lys Gly Ala Ala Glu Ser Ser Ser Lys
                 85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
        115                 120                 125

Thr Leu Ser Glu Ala Leu Arg Ile Ile Ala Gly Thr Leu Glu Val His
    130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220
```

-continued

```
Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Pro Pro Leu Pro Pro Pro Pro Gln Pro Pro Pro Leu Ala Ala
            260                 265                 270

Ala Gly Ala Ala Thr Ala Ala Thr Gly Gly Tyr Lys Val
        275                 280                 285


<210> SEQ ID NO 4
<211> LENGTH: 262
<212> TYPE: PRT
<213> ORGANISM: Phleum pratense

<400> SEQUENCE: 4

Ala Asp Ala Gly Tyr Ala Pro Ala Thr Pro Ala Ala Ala Gly Ala Ala
  1               5                  10                  15

Ala Gly Lys Ala Thr Thr Glu Glu Gln Lys Leu Ile Glu Lys Ile Asn
             20                  25                  30

Val Gly Phe Lys Ala Ala Val Ala Ala Arg Gln Pro Ala Ala Asp Lys
         35                  40                  45

Phe Lys Thr Phe Glu Ala Ala Ser Pro Arg His Pro Arg Pro Leu Arg
     50                  55                  60

Gln Gly Ala Gly Leu Val Ser Lys Leu Asp Ala Ala Tyr Ser Val Ala
 65                  70                  75                  80

Tyr Lys Ala Ala Val Gly Ala Thr Pro Glu Ala Lys Phe Asp Ser Phe
                 85                  90                  95

Val Ala Ser Leu Thr Glu Ala Leu Arg Val Ile Ala Gly Ala Leu Glu
            100                 105                 110

Val His Ala Val Lys Pro Val Thr Glu Glu Pro Gly Met Ala Lys Ile
        115                 120                 125

Pro Ala Gly Glu Leu Gln Ile Ile Asp Lys Ile Asp Ala Ala Phe Lys
    130                 135                 140

Val Ala Ala Thr Ala Ala Ala Thr Ala Pro Ala Asp Asp Lys Phe Thr
145                 150                 155                 160

Val Phe Glu Ala Ala Phe Asn Lys Ala Ile Lys Glu Ser Thr Gly Gly
                165                 170                 175

Ala Tyr Asp Thr Tyr Lys Cys Ile Pro Ser Leu Glu Ala Ala Val Lys
            180                 185                 190

Gln Ala Tyr Ala Ala Thr Val Ala Ala Ala Ala Glu Val Lys Tyr Thr
        195                 200                 205

Val Phe Glu Ala Ala Leu Thr Lys Ala Ile Thr Ala Met Ser Glu Val
    210                 215                 220

Gln Ser Lys Val Gln Pro Ala Thr Gly Ala Ala Thr Val Ala Ala Gly
225                 230                 235                 240

Ala Ala Thr Thr Ala Ala Gly Ala Ala Ser Gly Ala Ala Thr Val Ala
                245                 250                 255

Ala Gly Gly Tyr Lys Val
            260


<210> SEQ ID NO 5
<211> LENGTH: 309
<212> TYPE: PRT
<213> ORGANISM: Poa pratensis

<400> SEQUENCE: 5
```

-continued

Ala Asp Val Gly Tyr Gly Ala Pro Ala Thr Leu Ala Thr Pro Ala Thr
1 5 10 15

Pro Pro Ala Ala Pro Ala Ala Gly Tyr Thr Pro Ala Ala Pro Ala Gly
20 25 30

Ala Ala Pro Lys Ala Thr Thr Asp Glu Gln Lys Leu Ile Glu Lys Ile
35 40 45

Asn Ala Gly Phe Lys Ala Ala Val Ala Ala Ala Ala Gly Val Pro Ala
50 55 60

Val Asp Lys Tyr Lys Thr Phe Val Ala Thr Phe Gly Thr Ala Ser Asn
65 70 75 80

Lys Ala Phe Ala Glu Ala Leu Ser Thr Glu Pro Lys Gly Ala Ala Ala
85 90 95

Ala Ser Ser Asn Ala Val Leu Thr Ser Lys Leu Asp Ala Ala Tyr Lys
100 105 110

Leu Ala Tyr Lys Ser Ala Glu Gly Ala Thr Pro Glu Ala Lys Tyr Asp
115 120 125

Ala Tyr Val Ala Thr Leu Ser Glu Ala Leu Arg Ile Ile Ala Gly Thr
130 135 140

Leu Glu Val His Ala Val Lys Pro Ala Gly Glu Glu Val Lys Ala Ile
145 150 155 160

Pro Ala Gly Glu Leu Gln Val Ile Asp Lys Val Asp Ala Ala Phe Lys
165 170 175

Val Ala Ala Thr Ala Ala Asn Ala Ala Pro Ala Asn Asp Lys Phe Thr
180 185 190

Val Phe Glu Ala Ala Phe Asn Asp Ala Ile Lys Ala Ser Thr Gly Gly
195 200 205

Ala Tyr Gln Ser Tyr Lys Phe Ile Pro Ala Leu Glu Ala Ala Val Lys
210 215 220

Gln Ser Tyr Ala Ala Thr Val Ala Thr Ala Pro Ala Val Lys Tyr Ala
225 230 235 240

Val Phe Glu Thr Ala Leu Lys Lys Ala Ile Thr Ala Met Ser Gln Ala
245 250 255

Gln Lys Ala Ala Lys Pro Ala Ala Ala Val Thr Ala Thr Ala Thr Gly
260 265 270

Ala Val Gly Ala Ala Thr Gly Ala Val Gly Ala Ala Thr Gly Ala Ala
275 280 285

Thr Ala Ala Ala Gly Gly Tyr Lys Thr Gly Ala Ala Thr Pro Thr Ala
290 295 300

Gly Gly Tyr Lys Val
305

<210> SEQ ID NO 6
<211> LENGTH: 283
<212> TYPE: PRT
<213> ORGANISM: Poa pratensis

<400> SEQUENCE: 6

Ala Asp Leu Ser Tyr Gly Ala Pro Ala Thr Pro Ala Ala Pro Ala Ala
1 5 10 15

Gly Tyr Thr Pro Ala Ala Pro Ala Gly Ala Ala Pro Lys Ala Thr Thr
20 25 30

Asp Glu Gln Lys Met Ile Glu Lys Ile Asn Val Gly Phe Lys Ala Ala
35 40 45

Val Ala Ala Ala Gly Gly Val Pro Ala Ala Asn Lys Tyr Lys Thr Phe

-continued

```
     50                  55                  60

Val Ala Thr Phe Gly Ala Ala Ser Asn Lys Ala Phe Ala Glu Ala Leu
 65                  70                  75                  80

Ser Thr Glu Pro Lys Gly Ala Ala Ala Asp Ser Ser Lys Ala Ala Leu
                 85                  90                  95

Thr Ser Lys Leu Asp Ala Ala Tyr Lys Leu Ala Tyr Lys Ser Ala Glu
            100                 105                 110

Gly Ala Thr Pro Glu Ala Lys Tyr Asp Asp Tyr Val Ala Thr Leu Ser
        115                 120                 125

Glu Ala Leu Arg Ile Ile Ala Gly Thr Leu Glu Val His Gly Val Lys
    130                 135                 140

Pro Ala Ala Glu Glu Val Lys Ala Thr Pro Ala Gly Glu Leu Gln Val
145                 150                 155                 160

Ile Asp Lys Val Asp Ala Ala Phe Lys Val Ala Ala Thr Ala Ala Asn
                165                 170                 175

Ala Ala Pro Ala Asn Asp Lys Phe Thr Val Phe Glu Ala Ala Phe Asn
            180                 185                 190

Asp Ala Ile Lys Ala Ser Thr Gly Gly Ala Tyr Gln Ser Tyr Lys Phe
        195                 200                 205

Ile Pro Ala Leu Glu Ala Ala Val Lys Gln Ser Tyr Ala Ala Thr Val
    210                 215                 220

Ala Thr Ala Pro Ala Val Lys Tyr Ala Val Phe Glu Thr Ala Leu Lys
225                 230                 235                 240

Lys Ala Ile Thr Ala Met Ser Gln Ala Gln Lys Ala Ala Lys Pro Ala
                245                 250                 255

Ala Ala Ala Thr Gly Thr Ala Thr Ala Ala Val Gly Ala Ala Thr Gly
            260                 265                 270

Ala Ala Thr Ala Ala Ala Gly Gly Tyr Lys Val
        275                 280


<210> SEQ ID NO 7
<211> LENGTH: 301
<212> TYPE: PRT
<213> ORGANISM: Lolium perenne

<400> SEQUENCE: 7

Met Ala Val Gln Lys Tyr Thr Val Ala Leu Phe Leu Ala Val Ala Leu
  1               5                  10                  15

Val Ala Gly Pro Ala Ala Ser Tyr Ala Ala Asp Ala Gly Tyr Thr Pro
            20                  25                  30

Ala Ala Ala Ala Thr Pro Ala Thr Pro Ala Ala Thr Pro Ala Ala Ala
        35                  40                  45

Gly Gly Lys Ala Thr Thr Asp Glu Gln Lys Leu Leu Glu Asp Val Asn
     50                  55                  60

Ala Gly Phe Lys Ala Ala Val Ala Ala Ala Ala Asn Ala Pro Pro Ala
 65                  70                  75                  80

Asp Lys Phe Lys Ile Phe Glu Ala Ala Phe Ser Glu Ser Ser Lys Gly
                 85                  90                  95

Leu Leu Ala Thr Ser Ala Ala Lys Ala Pro Gly Leu Ile Pro Lys Leu
            100                 105                 110

Asp Thr Ala Tyr Asp Val Ala Tyr Lys Ala Ala Glu Gly Ala Thr Pro
        115                 120                 125

Glu Ala Lys Tyr Asp Ala Phe Val Thr Ala Leu Thr Glu Ala Leu Arg
    130                 135                 140
```

-continued

Val Ile Ala Gly Ala Leu Glu Val His Ala Val Lys Pro Ala Thr Glu
145 150 155 160

Glu Val Pro Ala Ala Lys Ile Pro Thr Gly Glu Leu Gln Ile Val Asp
165 170 175

Lys Ile Asp Ala Ala Phe Lys Ile Ala Ala Thr Ala Ala Asn Ala Ala
180 185 190

Pro Thr Asn Asp Lys Phe Thr Val Phe Glu Ser Ala Phe Asn Lys Ala
195 200 205

Leu Asn Glu Cys Thr Gly Gly Ala Tyr Glu Thr Tyr Lys Phe Ile Pro
210 215 220

Ser Leu Glu Ala Ala Val Lys Asp Ala Tyr Ala Ala Thr Val Ala Ala
225 230 235 240

Ala Pro Glu Val Lys Tyr Ala Val Phe Glu Ala Ala Leu Thr Lys Ala
245 250 255

Ile Thr Ala Met Thr Gln Ala Gln Lys Ala Gly Lys Pro Ala Ala Ala
260 265 270

Ala Ala Thr Gly Ala Ala Thr Val Ala Thr Gly Ala Ala Thr Ala Ala
275 280 285

Ala Gly Ala Ala Thr Ala Ala Ala Gly Gly Tyr Lys Ala
290 295 300

<210> SEQ ID NO 8
<211> LENGTH: 301
<212> TYPE: PRT
<213> ORGANISM: Lolium perenne

<400> SEQUENCE: 8

Met Ala Val Gln Lys Tyr Thr Val Ala Leu Phe Leu Ala Val Ala Leu
1 5 10 15

Val Ala Gly Pro Ala Ala Ser Tyr Ala Ala Asp Ala Gly Tyr Thr Pro
20 25 30

Ala Ala Ala Ala Thr Pro Ala Thr Pro Ala Ala Thr Pro Ala Ala Ala
35 40 45

Gly Gly Lys Ala Thr Thr Asp Glu Gln Lys Leu Leu Glu Asp Val Asn
50 55 60

Ala Gly Phe Lys Ala Ala Val Ala Ala Ala Ala Asn Ala Pro Pro Ala
65 70 75 80

Asp Ala Phe Lys Ile Phe Glu Ala Ala Phe Ser Glu Ser Ser Lys Gly
85 90 95

Leu Leu Ala Thr Ser Ala Ala Lys Ala Pro Gly Leu Ile Pro Lys Leu
100 105 110

Asp Thr Ala Tyr Asp Val Ala Tyr Lys Ala Ala Glu Gly Ala Thr Pro
115 120 125

Glu Ala Lys Tyr Asp Ala Phe Val Thr Ala Leu Thr Glu Ala Leu Arg
130 135 140

Val Ile Ala Gly Ala Leu Glu Val His Ala Val Lys Pro Ala Thr Glu
145 150 155 160

Glu Val Pro Ala Ala Lys Ile Pro Thr Gly Glu Leu Gln Ile Val Asp
165 170 175

Lys Ile Asp Ala Ala Phe Lys Ile Ala Ala Thr Ala Ala Asn Ala Ala
180 185 190

Pro Thr Asn Asp Lys Phe Thr Val Phe Glu Ser Ala Phe Asn Lys Ala
195 200 205

Leu Asn Glu Cys Thr Gly Gly Ala Tyr Glu Thr Tyr Lys Phe Ile Pro
210 215 220

-continued

```
Ser Leu Glu Ala Ala Val Lys Asp Ala Tyr Ala Ala Thr Val Ala Ala
225                 230                 235                 240

Ala Pro Glu Val Lys Tyr Ala Val Phe Glu Ala Ala Leu Thr Lys Ala
                245                 250                 255

Ile Thr Ala Met Thr Gln Ala Gln Lys Ala Gly Lys Pro Ala Ala Ala
            260                 265                 270

Ala Ala Thr Gly Ala Ala Thr Val Ala Thr Gly Ala Ala Thr Ala Ala
        275                 280                 285

Ala Gly Ala Ala Thr Ala Ala Ala Gly Gly Tyr Lys Ala
    290                 295                 300


<210> SEQ ID NO 9
<211> LENGTH: 301
<212> TYPE: PRT
<213> ORGANISM: Lolium perenne

<400> SEQUENCE: 9

Met Ala Val Gln Lys Tyr Thr Val Ala Leu Phe Leu Ala Val Ala Leu
  1               5                  10                  15

Val Ala Gly Pro Ala Ala Ser Tyr Ala Ala Asp Ala Gly Tyr Thr Pro
             20                  25                  30

Ala Ala Ala Ala Thr Pro Ala Thr Pro Ala Ala Thr Pro Ala Ala Ala
         35                  40                  45

Gly Gly Lys Ala Thr Thr Asp Glu Gln Lys Leu Leu Glu Asp Val Asn
     50                  55                  60

Ala Gly Phe Lys Ala Ala Val Ala Ala Ala Ala Asn Ala Pro Pro Ala
 65                  70                  75                  80

Asp Lys Phe Lys Ile Phe Glu Ala Ala Phe Ser Glu Ser Ser Lys Gly
                 85                  90                  95

Leu Leu Ala Thr Ser Ala Ala Lys Ala Pro Gly Leu Ile Pro Lys Leu
            100                 105                 110

Asp Thr Ala Tyr Asp Val Ala Tyr Lys Ala Ala Glu Gly Ala Thr Pro
        115                 120                 125

Glu Ala Lys Tyr Asp Ala Phe Val Thr Ala Leu Thr Glu Ala Leu Arg
    130                 135                 140

Val Ile Ala Gly Ala Leu Glu Val His Ala Val Lys Pro Ala Thr Glu
145                 150                 155                 160

Glu Val Pro Ala Ala Lys Ile Pro Thr Gly Glu Leu Gln Ile Val Asp
                165                 170                 175

Lys Ile Asp Ala Ala Phe Lys Ile Ala Ala Thr Ala Ala Asn Ala Ala
            180                 185                 190

Pro Thr Asn Asp Lys Phe Thr Val Phe Glu Ser Ala Phe Asn Lys Ala
        195                 200                 205

Leu Asn Glu Cys Thr Gly Gly Ala Tyr Glu Thr Tyr Lys Phe Ile Pro
    210                 215                 220

Ser Leu Glu Ala Ala Val Lys Asp Ala Tyr Ala Ala Thr Val Ala Ala
225                 230                 235                 240

Ala Pro Glu Val Lys Tyr Ala Val Phe Glu Ala Ala Leu Thr Lys Ala
                245                 250                 255

Ile Thr Ala Met Thr Gln Ala Gln Lys Ala Gly Lys Pro Ala Ala Ala
            260                 265                 270

Ala Ala Thr Gly Ala Ala Thr Val Ala Thr Gly Ala Ala Thr Ala Ala
        275                 280                 285

Ala Gly Ala Ala Thr Ala Ala Ala Gly Ala Tyr Ala Ala
```

-continued

```
    290                 295                 300


<210> SEQ ID NO 10
<211> LENGTH: 300
<212> TYPE: PRT
<213> ORGANISM: Lolium perenne

<400> SEQUENCE: 10

Met Ala Val Gln Lys Tyr Thr Val Ala Leu Phe Leu Ala Val Ala Leu
  1               5                  10                  15

Val Ala Gly Pro Ala Ala Ser Tyr Ala Ala Asp Ala Gly Tyr Thr Pro
             20                  25                  30

Ala Ala Ala Ala Thr Pro Ala Thr Pro Ala Ala Thr Pro Ala Ala Ala
         35                  40                  45

Gly Gly Lys Ala Thr Thr Asp Glu Gln Lys Leu Leu Glu Asp Val Asn
     50                  55                  60

Ala Gly Phe Lys Ala Ala Val Ala Ala Ala Ala Asn Ala Pro Pro Ala
 65                  70                  75                  80

Asp Lys Phe Lys Ile Phe Glu Ala Ala Phe Ser Glu Ser Ser Lys Gly
                 85                  90                  95

Leu Leu Ala Thr Ser Ala Ala Lys Ala Pro Gly Leu Ile Pro Lys Leu
            100                 105                 110

Asp Thr Ala Tyr Asp Val Ala Tyr Lys Ala Ala Glu Gly Ala Thr Pro
        115                 120                 125

Glu Ala Lys Tyr Asp Ala Phe Val Thr Ala Leu Thr Glu Ala Leu Arg
    130                 135                 140

Val Ile Ala Gly Ala Leu Glu Val His Ala Val Lys Pro Ala Thr Glu
145                 150                 155                 160

Glu Val Pro Ala Ala Lys Ile Pro Thr Gly Glu Leu Gln Ile Val Asp
                165                 170                 175

Lys Ile Asp Ala Ala Phe Lys Ile Ala Ala Thr Ala Ala Asn Ala Ala
            180                 185                 190

Pro Thr Asn Asp Lys Phe Thr Val Phe Glu Ser Ala Phe Asn Lys Ala
        195                 200                 205

Leu Asn Glu Cys Thr Gly Gly Ala Tyr Glu Thr Tyr Lys Phe Ile Pro
    210                 215                 220

Ser Leu Glu Ala Ala Val Lys Asp Ala Tyr Ala Ala Thr Val Ala Ala
225                 230                 235                 240

Ala Pro Glu Val Lys Tyr Ala Val Phe Glu Ala Ala Leu Thr Lys Ala
                245                 250                 255

Ile Thr Ala Met Thr Gln Ala Gln Lys Ala Gly Lys Pro Ala Ala Ala
            260                 265                 270

Ala Ala Thr Gly Ala Ala Thr Val Ala Thr Gly Ala Ala Thr Ala Ala
        275                 280                 285

Ala Gly Ala Ala Thr Ala Ala Ala Gly Tyr Lys Ala
    290                 295                 300


<210> SEQ ID NO 11
<211> LENGTH: 301
<212> TYPE: PRT
<213> ORGANISM: Lolium perenne

<400> SEQUENCE: 11

Met Ala Val Gln Lys Tyr Thr Val Ala Leu Phe Leu Ala Val Ala Leu
  1               5                  10                  15

Val Ala Gly Pro Ala Ala Ser Tyr Ala Ala Asp Ala Gly Tyr Thr Pro
```

-continued

```
            20                  25                  30

Ala Ala Ala Ala Thr Pro Ala Thr Pro Ala Ala Thr Pro Ala Ala Ala
        35                  40                  45

Gly Gly Lys Ala Thr Thr Asp Glu Gln Lys Leu Leu Glu Asp Val Asn
    50                  55                  60

Ala Gly Phe Lys Ala Ala Val Ala Ala Ala Ala Asn Ala Pro Pro Ala
 65                 70                  75                  80

Asp Lys Phe Lys Ile Phe Glu Ala Ala Phe Ser Glu Ser Ser Lys Gly
                85                  90                  95

Leu Leu Ala Thr Ser Ala Ala Lys Ala Pro Gly Leu Ile Pro Lys Leu
            100                 105                 110

Asp Thr Ala Tyr Asp Val Ala Tyr Lys Ala Ala Glu Gly Ala Thr Pro
        115                 120                 125

Glu Ala Lys Tyr Asp Ala Phe Val Thr Ala Leu Thr Glu Ala Leu Arg
    130                 135                 140

Val Ile Ala Gly Ala Leu Glu Val His Ala Val Lys Pro Ala Thr Glu
145                 150                 155                 160

Glu Val Pro Ala Ala Lys Ile Pro Thr Gly Glu Leu Gln Ile Val Asp
                165                 170                 175

Lys Ile Asp Ala Ala Phe Lys Ile Ala Ala Thr Ala Ala Asn Ala Ala
            180                 185                 190

Pro Thr Asn Asp Asn Leu Ala Ala Phe Glu Ser Ala Phe Asn Lys Ala
        195                 200                 205

Leu Asn Glu Cys Thr Gly Gly Ala Tyr Glu Thr Tyr Lys Phe Ile Pro
    210                 215                 220

Ser Leu Glu Ala Ala Val Lys Asp Ala Tyr Ala Ala Thr Val Ala Ala
225                 230                 235                 240

Ala Pro Glu Val Lys Tyr Ala Val Phe Glu Ala Ala Leu Thr Lys Ala
                245                 250                 255

Ile Thr Ala Met Thr Gln Ala Gln Lys Ala Gly Lys Pro Ala Ala Ala
            260                 265                 270

Ala Ala Thr Gly Ala Ala Thr Val Ala Thr Gly Ala Ala Thr Ala Ala
        275                 280                 285

Ala Gly Ala Ala Thr Ala Ala Ala Gly Gly Tyr Lys Ala
    290                 295                 300


<210> SEQ ID NO 12
<211> LENGTH: 301
<212> TYPE: PRT
<213> ORGANISM: Lolium perenne

<400> SEQUENCE: 12

Met Ala Val Gln Lys Tyr Thr Val Ala Leu Phe Leu Ala Val Ala Leu
  1               5                  10                  15

Val Ala Gly Pro Ala Ala Ser Tyr Ala Ala Asp Ala Gly Tyr Thr Pro
            20                  25                  30

Ala Ala Ala Ala Thr Pro Ala Thr Pro Ala Ala Thr Pro Ala Ala Ala
        35                  40                  45

Gly Gly Lys Ala Thr Thr Asp Glu Gln Lys Leu Leu Glu Asp Val Asn
    50                  55                  60

Ala Gly Phe Lys Ala Ala Val Ala Ala Ala Ala Asn Ala Pro Pro Ala
 65                 70                  75                  80

Asp Lys Phe Lys Ile Phe Glu Ala Ala Phe Ser Glu Ser Ser Lys Gly
                85                  90                  95
```

-continued

```
Leu Leu Ala Thr Ser Ala Ala Lys Ala Pro Gly Leu Ile Pro Lys Leu
            100                 105                 110

Asp Thr Ala Tyr Asp Val Ala Tyr Lys Ala Ala Glu Gly Ala Thr Pro
        115                 120                 125

Glu Ala Lys Tyr Asp Ala Phe Val Thr Ala Leu Thr Glu Ala Leu Arg
    130                 135                 140

Val Ile Ala Gly Ala Leu Glu Val His Ala Val Lys Pro Ala Thr Glu
145                 150                 155                 160

Glu Val Pro Ala Ala Lys Ile Pro Thr Gly Glu Leu Gln Ile Val Asp
                165                 170                 175

Lys Ile Asp Ala Ala Phe Lys Ile Ala Ala Thr Ala Ala Asn Ala Ala
            180                 185                 190

Pro Thr Asn Asp Lys Phe Thr Val Phe Glu Ser Ala Phe Asn Lys Ala
        195                 200                 205

Leu Asn Glu Cys Thr Gly Gly Ala Tyr Glu Thr Tyr Lys Phe Ile Pro
    210                 215                 220

Ser Leu Glu Ala Gly Ala Ala Asp Ala Tyr Ala Ala Thr Val Ala Ala
225                 230                 235                 240

Ala Pro Glu Val Lys Tyr Ala Val Phe Glu Ala Ala Leu Thr Lys Ala
                245                 250                 255

Ile Thr Ala Met Thr Gln Ala Gln Lys Ala Gly Lys Pro Ala Ala Ala
            260                 265                 270

Ala Ala Thr Gly Ala Ala Thr Val Ala Thr Gly Ala Ala Thr Ala Ala
        275                 280                 285

Ala Gly Ala Ala Thr Ala Ala Ala Gly Gly Tyr Lys Ala
    290                 295                 300


<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

cctccggcgg acgcgttcaa gatc                                            24


<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

gatcttgaac gcgtccgccg gagg                                            24


<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

gctgctggtg cctacgcagc ctgatcagc                                       29
```

-continued

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gctgatcagg ctgcgtaggc accagcagc 29

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ccaccgccgc tgcttgaggc tacaaagc 28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gctttgtagc ctcaagcagc ggcggtgg 28

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
ccaccaacga taacttggcc gccttcgaga gtgc 34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gcactctcga aggcggccaa gttatcgttg gtgg 34

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cctcgaggcc ggggccgcgc aggcctacg 29

<210> SEQ ID NO 22

-continued

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

cgtaggcctg cgcggccccg gcctcgagg                                   29
```